(12) United States Patent
Boylan et al.

(10) Patent No.: US 6,881,542 B1
(45) Date of Patent: Apr. 19, 2005

(54) SERINE THREONINE KINASE MEMBER, H2520-59

(75) Inventors: John F. Boylan, Thousand Oaks, CA (US); Alex J. Bowers, Simi Valley, CA (US)

(73) Assignee: Amgen Inc., Thousand Oaks, CA (US)

(*) Notice: Subject to any disclaimer, the term of this patent is extended or adjusted under 35 U.S.C. 154(b) by 123 days.

(21) Appl. No.: 09/909,474

(22) Filed: Jul. 19, 2001

Related U.S. Application Data

(60) Provisional application No. 60/219,204, filed on Jul. 19, 2000.

(51) Int. Cl.⁷ ............... C12Q 1/68; C12N 15/00; C12N 5/00; C12N 9/20; C07H 21/04
(52) U.S. Cl. ............... 435/6; 435/194; 435/252.3; 435/325; 435/320.1; 536/23.2
(58) Field of Search ............... 435/6, 194, 320.1, 435/325, 252.3, 69.1; 536/23.2, 23.1

(56) References Cited

U.S. PATENT DOCUMENTS

| | | | |
|---|---|---|---|
| 6,387,676 B1 * | 5/2002 | Virca et al. | 435/194 |
| 2002/0197679 A1 * | 12/2002 | Tang et al. | 435/69.1 |

FOREIGN PATENT DOCUMENTS

| | | |
|---|---|---|
| WO | WO 00/08180 | 2/2000 |
| WO | WO 00/55350 | 9/2000 |

OTHER PUBLICATIONS

Hanks et al., "The protein kinase family: conserved features and deduced phylogeny of the catalytic domains", *Science* 241:42–52, 1988.

Cross et al., "Serine/threonine protein kinases and apoptosis", *Exp Cell Res* 256:34–41, 2000.

Mayumi–Matsuda et al., "Identification of a novel kinase–like gene induced during neuronal cell death", *Biochem Biophys Res Comm* 258: 260–264, 1999.

Database GenBank. National Library of Medicine, (Bethesda, Maryland, US), AN AL034548, Blakey, Human DNA sequence from clone RP5–1103G7 on chromosome 20p12.2–13, 2001.

Database GenBank. National Library of Medicine, (Bethesda, Maryland, US), AN AK026945, Kawabata et al., Homo sapiens cDNA: FLJ23292 fis, clone HEP10334, NEDO human cDNA sequencing project, 2000.

Seher and Leptin, "Tribbles, a cell–cycle brake that coordinates proliferation and morphogenesis during *Drosophila* gastrulation", *Curr Biol* 10:623–629, 2000.

Mata et al., "Tribbles coordinates mitosis and morphogenesis in *Drosophila* by regulating string/cdc25 proteolysis", *Cell* 101:511–522, 2000.

Großhans and Wieschaus, "A genetic link between morphogenesis and cell division during formation of the ventral furrow in *Drosophila*", *Cell* 101:523–531, 2000.

* cited by examiner

*Primary Examiner*—Maryam Monshipouri
(74) *Attorney, Agent, or Firm*—Marshall, Gerstein & Borun LLP

(57) ABSTRACT

The present invention relates to a serine threonine kinase. The invention also relates to nucleic acids encoding the kinase, vectors, host cells, antibodies and recombinant methods for producing the h2520-59 polypeptide. In addition, the invention discloses therapeutic, diagnostic and research utilities for h2520-59 and related products.

17 Claims, 5 Drawing Sheets

Figure 1a
hAMGEN2520-59 Coding region and amino acid sequence.

Seq ID NO:

```
           10         20         30         40         50         60
1  ATGCGAGCCACCCCTCTGGCTGCTCCTGCGGGTTCCCTGTCCAGGAAGAAGCGGTTGGAG
2  M  R  A  T  P  L  A  A  P  A  G  S  L  S  R  K  K  R  L  E
           70         80         90        100        110        120
   TTGGATGACAACTTAGATACCGAGCGTCCCGTCCAGAAACGAGCTCGAAGTGGGCCCCAG
   L  D  D  N  L  D  T  E  R  P  V  Q  K  R  A  R  S  G  P  Q
          130        140        150        160        170        180
   CCCAGACTGCCCCCCTGCCTGTTGCCCCTGAGCCCACCTACTGCTCCAGATCGTGCAACT
   P  R  L  P  P  C  L  L  P  L  S  P  P  T  A  P  D  R  A  T
          190        200        210        220        230        240
   GCTGTGGCCACTGCCTCCCGTCTTGGGCCCTATGTCCTCCTGGAGCCCGAGGAGGGCGGG
   A  V  A  T  A  S  R  L  G  P  Y  V  L  L  E  P  E  E  G  G
          250        260        270        280        290        300
   CGGGCCTACCGGGCCCTGCACTGCCCTACAGGCACTGAGTATACCTGCAAGGTGTACCCC
   R  A  Y  R  A  L  H  C  P  T  G  T  E  Y  T  C  K  V  Y  P
          310        320        330        340        350        360
   GTCCAGGAAGCCCTGGCCGTGCTGGAGCCCTACGCGCGGCTGCCCCCGCACAAGCATGTG
   V  Q  E  A  L  A  V  L  E  P  Y  A  R  L  P  P  H  K  H  V
          370        380        390        400        410        420
   GCTCGGCCCACTGAGGTCCTGGCTGGTACCCAGCTCCTCTACGCCTTTTTCACTCGGACC
   A  R  P  T  E  V  L  A  G  T  Q  L  L  Y  A  F  F  T  R  T
          430        440        450        460        470        480
   CATGGGGACATGCACAGCCTGGTGCGAAGCCGCCACCGTATCCCTGAGCCTGAGGCTGCC
   H  G  D  M  H  S  L  V  R  S  R  H  R  I  P  E  P  E  A  A
          490        500        510        520        530        540
   GTGCTCTTCCGCCAGATGGCCACCGCCCTGGCGCACTGTCACCAGCACGGTCTGGTCCTG
   V  L  F  R  Q  M  A  T  A  L  A  H  C  H  Q  H  G  L  V  L
          550        560        570        580        590        600
   CGTGATCTCAAGCTGTGTCGCTTTGTCTTCGCTGACCGTGAGAGGAAGAAGCTGGTGCTG
   R  D  L  K  L  C  R  F  V  F  A  D  R  E  R  K  K  L  V  L
          610        620        630        640        650        660
   GAGAACCTGGAGGACTCCTGCGTGCTGACTGGGCCAGATGATTCCCTGTGGGACAAGCAC
   E  N  L  E  D  S  C  V  L  T  G  P  D  D  S  L  W  D  K  H
          670        680        690        700        710        720
   GCCGTGCCCAGCCTACGTGGGACCTGAGATACTCAGCTCACGGGCCTCATACTCGGGCAAG
   A  C  P  A  Y  V  G  P  E  I  L  S  S  R  A  S  Y  S  G  K
          730        740        750        760        770        780
   GCAGCCGATGTCTGGAGCCTGGGCGTGGCGCTCTTCACCATGCTGGCCGGCCACTACCCC
   A  A  D  V  W  S  L  G  V  A  L  F  T  M  L  A  G  H  Y  P
          790        800        810        820        830        840
   TTCCAGGACTCGGAGCCTGTCCTGCTCTTCGGCAAGATCCGCCGCGGGGCCTACGCCTTG
   F  Q  D  S  E  P  V  L  L  F  G  K  I  R  R  G  A  Y  A  L
          850        860        870        880        890        900
   CCTGCAGGCCTCTCGGCCCCTGCCCGCTGTCTGGTTCGCTGCCTCCTTCGTCGGGAGCCA
   P  A  G  L  S  A  P  A  R  C  L  V  R  C  L  L  R  R  E  P
```

Figure 1b
hAMGEN2520-59 Coding region and amino acid sequence (continued).

Seq ID NO:

```
            910       920       930       940       950       960
1 GCTGAACGGCTCACAGCCACAGGCATCCTCCTGCACCCCTGGCTGCGACAGGACCCGATG
2  A  E  R  L  T  A  T  G  I  L  L  H  P  W  L  R  Q  D  P  M
            970       980       990      1000      1010      1020
  CCCTTAGCCCCAACCCGATCCCATCTCTGGGAGGCTGCCCAGGTGGTCCCTGATGGACTG
   P  L  A  P  T  R  S  H  L  W  E  A  A  Q  V  V  P  D  G  L
           1030      1040      1050      1060      1070
  GGGCTGGACGAAGCCAGGGAAGAGGAGGGAGACAGAGAAGTGGTTCTGTATGGCTAG
   G  L  D  E  A  R  E  E  E  G  D  R  E  V  V  L  Y  G
```

Figure 2a

```
                              1                                                   50
2520-59               (1)     --------------------------------------------------
Genbank BAB15597      (1)     --------------------------------------------------
Patented Seq: NO 1367 (1)     LRFASPGPGAGRARDSQRKWRRLRARPLLGPGQGWSWAGIPSSAAAQRAG
Patented SEQ ID NO:1102 (1)   --------------------------------------------------
JJ503-KS              (1)     --------------------------------------------------
Consensus             (1)     -----------------------------GQGWSWAGIPSSAAAQRAG 51                                                  100
2520-59               (1)     --------------------------------------------------
Genbank BAB15597      (1)     --------------------------------------------------
Patented Seq: NO 1367 (51)    --------------------MRATPLAAPAGSLSRKKKRLELDDNLDT
Patented SEQ ID NO:1102 (1)   --------------------MRATPLAAPAGSLSRKKKRLELDDNLDT
JJ503-KS              (20)    PPAGALEALSPGGARAHAERRGEMRATPLAAPAGSLSRKKKRLELDDNLDT
Consensus             (51)    --------------------MRATPLAAPAGSLSRKKKRLELDDNLDT 101                                                 150
2520-59               (28)    ERPVQKRARSGPQPRLPPCLLPLSPPTAPDRATAVATASRLGPYVLLEPE
Genbank BAB15597      (28)    ERPVQKRARSGPQPRLPPCLLPLSPPTAPDRATAVATASRLGPYVLLEPE
Patented Seq: NO 1367 (101)   ERPVQKRARSGPQPRLPPCLLPLSPPTAPDRATAVXTXSRXXXYVLLEAR
Patented SEQ ID NO:1102 (1)   --------------------------------------------------
JJ503-KS              (70)    ERPVQKRARSGPQPRLPPCLLPLSPPTAPDRATAVATASRLGPYVLLEPE
Consensus             (101)   ERPVQKRARSGPQPRLPPCLLPLSPPTAPDRATAVATASRLGPYVLLEPE
```

Figure 2b

```
                              151                                                    200
         2520-59        (78)  EGGGRAYRALHCPTGTEYTCKVYPVQEALAVLEPYARLPPHKHVARPTEVL
Genbank BAB15597        (78)  EGGGRAYQALHCPTGTEYTCKVYPVQEAPAVLEPYARLPPHKHVARPTEVL
Patented Seq: NO 1367  (151)  RXA-----------------------------------------------GP
Patented SEQ ID NO:1102  (1)  --------------------------------------------------
        JJ503-KS       (120)  EGGGRAYQALHCPTGTEYTCKVYPVQEALAVLEPYARLPPHKHVARPTEVL
        Consensus      (151)  EGGGRAYQALHCPTGTEYTCKVYPVQEA AVLEPYARLPPHKHVARPTEVL 201                                                    250
         2520-59       (128)  AGTQLLYAFFTRTHGDMHSLVRSRHRIPEPEAAVLFRQMATALAHCHQHG
Genbank BAB15597       (128)  AGTQLLYAFFTRTHGDMHSLVRSRHRIPEPEAAVLFRQMATALAHCHQHG
Patented Seq: NO 1367  (154)  --------------------------------------------------
Patented SEQ ID NO:1102  (3)  GWYPAPLRLFHSDPWGHAQPGAKRHRIPEPEAAVLFRQMATALAHCHQHG
        JJ503-KS       (170)  AGTQLLYAFFTRTHGDMHSLVRSRHRIPEPEAAVLFRQMATALAHCHQHG
        Consensus      (201)  AGTQLLYAFFTRTHGDMHSLVRSRHRIPEPEAAVLFRQMATALAHCHQHG 251                                                    300
         2520-59       (178)  LVLRDLKLCRFVFADRERKKLVLENLEDSCVLTGPDDSLWDKHACPAYVG
Genbank BAB15597       (178)  LVLRDLKLCRFVFADRERKKLVLENLEDSCVLTGPDDSLWDKHACPAYVG
Patented Seq: NO 1367  (154)  --------------------------------------------------
Patented SEQ ID NO:1102 (53)  LVLRDLKLCRFVFADRERKKLVLENLEDSCVLTGPDDSLWDKHACPAYVG
        JJ503-KS       (220)  LVLRDLKLCRFVFADRERKKLVLENLEDSCVLTGPDDSLWDKHACPAYVG
        Consensus      (251)  LVLRDLKLCRFVFADRERKKLVLENLEDSCVLTGPDDSLWDKHACPAYVG 301                                                    350
         2520-59       (228)  PEILSSRASYSGKAADVWSLGVALFTMLAGHYPFQDSEPVLLFGKIRRGA
Genbank BAB15597       (228)  PEILSSRASYSGKAADVWSLGVALFTMLAGHYPFQDSEPVLLFGKIRRGA
Patented Seq: NO 1367  (154)  --------------------------------------------------
Patented SEQ ID NO:1102(103)  PEILSSRASYSGKAADVWSLGVALFTMLAGHYPFQDSEPVLLFGKIRRGA
        JJ503-KS       (270)  PEILSSRASYSGKAADVWSLGVALFTMLAGHYPFQDSEPVLLFGKIRRGA
        Consensus      (301)  PEILSSRASYSGKAADVWSLGVALFTMLAGHYPFQDSEPVLLFGKIRRGA
```

Figure 2c

```
                                351
            2520-59       (278) YALPAGLSAPARCLVRCLLRREPAERLTATGILLHPWLRQDPMPLAPTRS
   Genbank BAB15597       (278) YALPAGLSAPARCLVRCLLRREPAERLTATGILLHPWLRQDPMPLAPTRS
Patented Seq: NO 1367     (154) ------------------------------------------------
Patented SEQ ID NO:1102   (153) YALPAGLSAPARCLVRCLLRREPAERLTATGILLHPWLRQD--------
            JJ503-KS      (320) YALPAGLSAPARCLVRCLLRREPAERLTATGILLHPWLRQD--------
            Consensus     (351) YALPAGLSAPARCLVRCLLRREPAERLTATGILLHPWLRQDPMPLAPTRS
                                401                            431
            2520-59       (328) HLWEAAQVVPDGLGLDEAREEEGDREVVLYG
   Genbank BAB15597       (328) HLWEAAQVVPDGLGLDEAREEEGDREVVLYG
Patented Seq: NO 1367     (154) -------------------------------
Patented SEQ ID NO:1102   (203) HLWEAAQVVPDGLGLDEAREEEGDREVVLYG
            JJ503-KS      (361) -------------------------------
            Consensus     (401) HLWEAAQVVPDGLGLDEAREEEGDREVVLYG
```

SERINE THREONINE KINASE MEMBER, H2520-59

This application claims benefit of U.S. Provisional Application Ser. No. 60/219,204 filed Jul. 19, 2000, which is incorporated herein by reference in its entirety.

FIELD OF THE INVENTION

The present invention relates to a novel human serine threonine kinase family member (h2520-59), and uses thereof. The invention also relates to vectors, host cells, selective binding agents, such as antibodies, and methods for producing h2520-59 polypeptides. Also provided for are methods for the diagnosis, treatment, amelioration and/or prevention of diseases associated with h2520-59 polypeptides.

BACKGROUND OF THE INVENTION

Technical advances in identification, cloning, expression and manipulation of nucleic acid molecules and deciphering of the human genome have greatly accelerated discovery of novel therapeutics based upon deciphering of the human genome. Rapid nucleic acid sequencing techniques can now generate sequence information at unprecedented rates and, coupled with computational analyses, allow the assembly of overlapping sequences into the partial and entire genomes as well as identification of polypeptide-encoding regions. A comparison of a predicted amino acid sequence against a database compilation of known amino acid sequences allows one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides to create variants and derivatives thereof may confer advantageous properties on a product for use as a therapeutic.

In spite of significant technical advances in genome research over the past decade, the potential for development of novel therapeutics based on the human genome is still largely unrealized. Many genes encoding potentially beneficial polypeptide therapeutics, or those encoding polypeptides which may act as "targets" for therapeutic molecules, have still not been identified.

Accordingly, it is an object of the invention to identify novel polypeptides and nucleic acid molecules encoding the same which have diagnostic or therapeutic benefit.

Protein phosphorylation at specific amino acid residues is an important biological theme involved in the regulation of most cellular processes including cell cycle progression and division, signal transduction, and apoptosis. Site-specific phosphorylation can either activate or inactivate protein functions helping to link the extracellular environmental information to intracellular processes. Protein kinases represent a large and diverse group of enzymes with current estimates of around 2,000 members. Included in this family are many subgroups encoding oncogenes, growth factor receptors, signal transduction intermediates, apoptosis related kinases, and cyclin dependent kinases. Given the importance and diversity of protein kinase function, it is not surprising that alterations in phosphorylation are associated with many disease states such as cancer, diabetes, arthritis, and hypertension.

Serine-threonine kinases (ser/thr kinases) are a large sub-family of protein kinases which specifically phosphorylate serine and threonine residues. All ser/thr kinase family members contain a 250 amino acid catalytic domain which enzymatically transfers a phosphate group from an ATP molecule to a hydroxyl group on a serine or threonine side chain of a protein. (Hanks et al., Science 241: 42–52, 1988).

A number of ser/thr kinase family members are involved in tumor growth or cellular transformation by either increasing cellular proliferation or decreasing the rate of apoptosis. For example, the mitogen-activated protein kinases (MAPKs) are ser/thr kinases which act as intermediates within the signaling cascades of both growth/survival factors, such as EGF, and death receptors, such as the TNF receptor. Expression of ser/thr kinases, such as protein kinase A, protein kinase B and protein kinase C, have been shown be elevated in some tumor cells. Further, cyclin dependent kinases (cdk) are ser/thr kinases that play an important role in cell cycle regulation. Increased expression or activation of these kinases may cause uncontrolled cell proliferation leading to tumor growth. (See Cross et al., *Exp. Cell Res.* 256: 34–41, 2000).

Thus, identification of members of the ser/thr kinase family has led to a better understanding of cell proliferation, differentiation and survival. Identification of the novel ser/thr kinase gene and polypeptide, as described herein, will further clarify the understanding of these processes and facilitate the development of therapies for pathological conditions which involve cellular hyperproliferation and other biological processes.

SUMMARY OF THE INVENTION

The present invention relates to a novel serine/threonine kinase family and uses thereof. More specifically, the present invention relates to novel h2520-59 nucleic acid molecules and encoded polypeptides, and uses thereof.

The invention provides for an isolated nucleic acid molecule comprising a nucleotide sequence selected from the group consisting of:

(a) the nucleotide sequence set forth in SEQ ID NO: 1;
(b) the h2520-59 encoding portion of SEQ ID NO: 1 comprising nucleotides 49-1122 of SEQ ID NO 1;
(c) a nucleotide sequence encoding the polypeptide set forth in SEQ ID NO: 2;
(d) a nucleotide sequence which hybridizes under moderately or highly stringent conditions to the complement of (a) or (b) or (c), wherein the encoded polypeptide has an activity of the polypeptide set forth in SEQ ID NO: 2; and
(e) a nucleotide sequence complementary to any of (a)–(d).

The invention also provides for an isolated nucleic acid molecule comprising a nucleotide sequence selected from the group consisting of:

(a) a nucleotide sequence encoding a polypeptide that exhibits at least about 70, 75, 80, 85, 90, 95, 96, 97, 98, or 99 percent identity to the polypeptide set forth in SEQ ID NO: 2, wherein the polypeptide has an activity of the encoded polypeptide set forth in SEQ ID NO: 2 as determined using a computer program selected from the group consisting of GAP, BLASTP, BLASTN, FASTA, BLASTA, BLASTX, BestFit, and the Smith-Waterman algorithm;
(b) a nucleotide sequence encoding an allelic variant or splice variant of the nucleotide sequence set forth in SEQ ID NO: 1, wherein the encoded polypeptide has an activity of the polypeptide set forth in SEQ ID NO: 2;
(c) a nucleotide sequence of SEQ ID NO: 1, (a), or (b) encoding a polypeptide fragment of at least about 25 amino acid residues, wherein the polypeptide has an activity of the polypeptide set forth in SEQ ID NO: 2;

(d) a nucleotide sequence encoding a polypeptide that has a substitution and/or deletion of 1 to 358 amino acid residues set forth in SEQ ID NO: 2 wherein the encoded polypeptide has an activity of the polypeptide set forth in SEQ ID NO: 2;

(e) a nucleotide sequence of SEQ ID NO: 1, or (a–(d) comprising a fragment of at least about 16 nucleotides;

(f) a nucleotide sequence which hybridizes under moderately or highly stringent conditions to the complement of any of (a)–(e), wherein the encoded polypeptide has an activity of the polypeptide set forth in SEQ ID NO: 2; and (g) a nucleotide sequence complementary to any of (a)–(f).

The invention further provides for an isolated nucleic acid molecule comprising a nucleotide sequence selected from the group consisting of:

(a) a nucleotide sequence encoding a polypeptide set forth in SEQ ID NO: 2 with at least one conservative amino acid substitution, wherein the encoded polypeptide has an activity of the polypeptide set forth in SEQ ID NO: 2;

(b) a nucleotide sequence encoding a polypeptide set forth in SEQ ID NO: 2 with at least one amino acid insertion, wherein the encoded polypeptide has an activity of the polypeptide set forth in SEQ ID NO: 2;

(c) a nucleotide sequence encoding a polypeptide set forth in SEQ ID NO: 2 with at least one amino acid deletion, wherein the encoded polypeptide has an activity of the polypeptide set forth in SEQ ID NO: 2;

(d) a nucleotide sequence encoding a polypeptide set forth in SEQ ID NO: 2 which has a C- and/or N-terminal truncation, wherein the encoded polypeptide has an activity of the polypeptide set forth in SEQ ID NO: 2;

(e) a nucleotide sequence encoding a polypeptide set forth in SEQ ID NO: 2 with at least one modification selected from the group consisting of amino acid substitutions, amino acid insertions, amino acid deletions, C-terminal truncation, and N-terminal truncation, wherein the polypeptide has an activity of the encoded polypeptide set forth in SEQ ID NO: 2;

(f) a nucleotide sequence of (a)–(e) comprising a fragment of at least about 16 nucleotides;

(g) a nucleotide sequence which hybridizes under moderately or highly stringent conditions to the complement of any of (a)–(f) wherein the encoded polypeptide has an activity of the polypeptide set forth in SEQ ID NO: 2; and (h) a nucleotide sequence complementary to any of (a)–(e).

The invention also provides for an expression vector comprising the isolated nucleic acid molecules set forth herein; recombinant host cells (eukaryotic and/or prokaryotic) that comprise the vector; the process for producing a h2520 polypeptide comprising culturing the host cell under suitable conditions to express the polypeptide and optionally isolating the polypeptide from the culture; and the isolated polypeptide produced by this process. The nucleic acid molecule used in this process may also comprise promoter DNA other than the promoter DNA for the native h2520-59 polypeptide operatively linked to the nucleotide sequence encoding the h2520-59 polypeptide.

The invention also provides for a nucleic acid molecule as described in the previous paragraphs wherein the percent identity is determined using a computer program selected from the group consisting of GAP, BLASTP, BLASTN, FASTA, BLASTA, BLASTX, BestFit, and the Smith-Waterman algorithm.

The present invention provides a process for identifying candidate inhibitors and/or stimulators of h2520-59 polypeptide activity or production comprising exposing a host cell to the candidate inhibitors and/or stimulators, measuring h2520 polypeptide activity or production in the host cell, and comparing this activity with control cells (i.e., cells not exposed to the candidate inhibitor and/or stimulator). In a related aspect, the invention provides for the inhibitors and/or stimulators identified by any of the preceding methods.

The invention also provides for an isolated polypeptide comprising the amino acid sequence set forth in SEQ ID NO: 2.

The invention provides for an isolated polypeptide comprising the amino acid sequence selected from the group consisting of:

(a) the mature amino acid sequence set forth in SEQ ID NO: 2 comprising a mature amino terminus at residue 1, and optionally further comprising an amino-terminal methionine;

(b) an amino acid sequence for an ortholog of SEQ ID NO: 2, wherein the polypeptide has an activity of the polypeptide set forth in SEQ ID NO: 2;

(c) an amino acid sequence that exhibits at least about 70, 75, 80, 85, 90, 95, 96, 97, 98, or 99 percent identity to the amino acid sequence of SEQ ID NO: 2, wherein the polypeptide has an activity of the polypeptide set forth in SEQ ID NO: 2 as determined using a computer program selected from the group consisting of GAP, BLASTP, BLASTN, FASTA, BLASTA, BLASTX, BestFit, and the Smith-Waterman algorithm;

(d) a fragment of the amino acid sequence set forth in SEQ ID NO: 2 comprising at least about 25 amino acid residues, wherein the polypeptide has an activity of the polypeptide set forth in SEQ ID NO: 2; and (e) an amino acid sequence for an allelic variant or splice variant of either the amino acid sequence set forth in SEQ ID NO: 2, or at least one of (a)–(c), wherein the polypeptide has an activity of the polypeptide set forth in SEQ ID NO: 2.

The invention further provides for an isolated polypeptide comprising the amino acid sequence selected from the group consisting of:

(a) the amino acid sequence set forth in SEQ ID NO: 2 with at least one conservative amino acid substitution, wherein the polypeptide has an activity of the polypeptide set forth in SEQ ID NO: 2;

(b) the amino acid sequence set forth in SEQ ID NO: 2 with at least one amino acid insertion, wherein the polypeptide has an activity of the polypeptide set forth in SEQ ID NO: 2;

(c) the amino acid sequence set forth in SEQ ID NO: 2 with at least one amino acid deletion, wherein the polypeptide has an activity of the polypeptide set forth in SEQ ID NO:2;

(d) the amino acid sequence set forth in SEQ ID NO: 2 which has a C- and/or N-terminal truncation, wherein the polypeptide has an activity of the polypeptide set forth in SEQ ID NO: 2; and (e) the amino acid sequence set forth in SEQ ID NO: 2, with at least one modification selected from the group consisting of amino acid substitutions, amino acid insertions, amino acid deletions, C-terminal truncation, and N-terminal truncation, wherein the polypeptide has an activity of the polypeptide set forth in SEQ ID NO: 2.

Analogs of h2520-59 are provided for in the present invention which result from conservative and non-conservative amino acid substitutions of the h2520-59 polypeptide of SEQ ID NO: 2. Such analogs include a h2520-59 polypeptide wherein the amino acid corresponding to position 31 of SEQ ID NO: 2 is valine, isoleucine, methionine, leucine, phenylalanine, alanine, or norleucine; a h2520-59 polypeptide wherein the amino acid corresponding to position 60 of SEQ ID NO: 2 is threonine or serine; a h2520-59 polypeptide wherein the amino acid corresponding to position 229 of SEQ ID NO: 2 is glutamic acid or aspartic acid; a h2520-59 polypeptide wherein the amino acid corresponding to position 258 of SEQ ID NO: 2 is histidine, asparagine, glutamine, lysine, or arginine; a h2520-59 polypeptide wherein the amino acid corresponding to position 283 of SEQ ID NO: 2 is glycine, proline, or alanine; and a h2520-59 polypeptide wherein the amino acid corresponding to position 314 of SEQ ID NO: 2 is tryptophan, tyrosine, or phenylalanine.

The present invention also provides for an isolated polypeptide encoded by the nucleic acid molecules set forth herein.

The present invention further provides for an antibody or fragment thereof that specifically binds an h2520-59 polypeptide as set forth herein. This antibody can be polyclonal or monoclonal, and can be produced by immunizing an animal with a peptide comprising an amino acid sequence of SEQ ID NO: 2.

Also provided is the hybridoma that produces a monoclonal antibody that binds to a peptide comprising an amino acid sequence of SEQ ID NO: 2.

The present invention also provides for a method of detecting or quantitating the amount of h2520-59 polypeptide in a sample comprising contacting a sample suspected of containing h2520-59 polypeptide with the anti-h2520-59 antibody or antibody fragment set forth herein and detecting the binding of said antibody or antibody fragment.

Additionally provided by the invention are selective binding agents or fragments thereof that are capable of specifically binding the h2520-59 polypeptides, derivatives, variants, and fragments (preferably having sequences of at least about 25 amino acids) thereof. These selective binding agents may be antibodies such as humanized antibodies, human antibodies, polyclonal antibodies, monoclonal antibodies, chimeric antibodies, complementarity determining region (CDR)-grafted antibodies, anti-idiotypic antibodies, and fragments thereof. Furthermore, the selective binding agents may be antibody variable region fragments, such as Fab or Fab' fragments, or fragments thereof, and may comprise at least one complementarity determining region with specificity for a h2520-59 polypeptide set forth herein. The selective binding agent may also be bound to a detectable label, such as a radiolabel, a fluorescent label, an enzyme label, or any other label known in the art. Further, the selective binding agent may antagonize h2520-59 polypeptide biological activity, and/or be produced by immunizing an animal with a h2520-59 polypeptide as set forth herein.

The present invention also provides for a hybridoma that produces a selective binding agent capable of binding h2520-59 polypeptide as set forth herein.

Also provided is a method for treating, preventing, or ameliorating a disease, condition, or disorder comprising administering to a patient an effective amount of a selective binding agent as set forth herein. An effective amount, or a therapeutically effective amount, is an amount sufficient to result in a detectable change in the course or magnitude of the disease, condition or disorder, such as the intensity or duration of presentment of any symptom associated therewith.

Pharmaceutical compositions comprising the above-described nucleic acid molecules, polypeptides, or selective binding agents and one or more pharmaceutically acceptable formulation agents are also encompassed by the invention. The pharmaceutically acceptable formulation agent may be a carrier, adjuvant, solubilizer, stabilizer, or anti-oxidant. The nucleic acid molecules of the present invention may be contained in viral vectors. The pharmaceutical compositions are used to provide therapeutically effective amounts of the nucleic acid molecules or polypeptides of the present invention.

Also provided are derivatives of the h2520-59 polypeptides of the present invention. These polypeptides may be covalently modified with a water-soluble polymer wherein the water-soluble polymer is selected from the group consisting of polyethylene glycol, monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, and polyvinyl alcohol.

The present invention also provides for fusion polypeptides comprising the polypeptide sequences set forth herein fused to a heterologous amino acid sequence, which may be an IgG constant domain or fragment thereof.

Methods for treating, preventing or ameliorating a medical condition, such as cancer, in a mammal resulting from increased levels of h2520-59 polypeptide are also included in the present invention. These methods include administering to a patient a therapeutically effective amount of an antagonist selected from the group consisting of selective binding agents, small molecules, peptides, peptide derivatives and antisense oligonucleotides. The cancer may include lung cancer, colon cancer or breast cancer.

Methods for treating, preventing or ameliorating a medical condition in a mammal resulting from decreased levels of h2520-59 polypeptide are also included in the present invention. These methods comprise administering to a patient a therapeutically effective amount of a h2520-59 polypeptide; a nucleic acid molecule encoding a h2520-59 polypeptide; or a nucleic acid molecule comprising elements that regulate or modulate the expression of a h2520-59 polypeptide. Examples of these methods include gene therapy and cell therapy and are further described herein.

The invention encompasses methods of diagnosing a pathological condition or a susceptibility to a pathological condition in a subject caused by or resulting from abnormal levels of h2520-59 polypeptide comprising determining the presence or amount of expression of the h2520-59 polypeptide in a biological, tissue, or cellular sample; and comparing the level of said polypeptide in a biological, tissue, or cellular sample from either normal subjects or the subject at a different time, wherein susceptibility to a pathological condition is based on the presence or amount of expression of the polypeptide.

The invention also provides for devices comprising a membrane suitable for implantation to administer a h2520-59 polypeptide, wherein h2520-59 polypeptide or cells which can secrete said peptide may be encapsulated in the membrane. The said membrane is permeable to the h2520-59 polypeptide; preferably, the membrane is impermeable to detrimental materials such as materials larger than the polypeptide.

The present invention also provides a method of identifying compounds which bind to a h2520-59 polypeptide. The method comprises contacting a h2520-59 polypeptide with a test molecule and determining the extent of binding of the test molecule to the polypeptide. The method may further comprise determining whether such test molecules are agonists or antagonists of a h2520-59 polypeptide. The present invention further provides a method of testing the impact of molecules on the expression of h2520-59 polypeptide or on the activity of h2520-59 polypeptide.

The present invention further provides a method of modulating levels of a h2520-polypeptide in an animal comprising administering to the animal the nucleic acid molecule set forth herein.

A transgenic non-human animal comprising a nucleic acid molecule encoding a h2520-59 polypeptide is also encompassed by the invention. The h2520-59 nucleic acid molecule is introduced into the animal in a manner that allows expression and increased levels of the h2520-59 polypeptide, which may include increased circulating levels. The transgenic non-human animal is preferably a mammal.

The present invention provides for a diagnostic reagent comprising a detectably labeled polynucleotide encoding the amino acid sequence set out in SEQ ID NO: 2, or a fragment, variant or homolog thereof, including allelic variants and spliced variants thereof. The detectably labeled polynucleotide may be a first-strand cDNA, DNA, or RNA.

The invention also provides a method for detecting the presence of h2520-59 nucleic acid molecules in a biological sample comprising the steps of.

(a) providing a biological sample suspected of containing h2520-59 nucleic acid molecules;

(b) contacting the biological sample with a diagnostic reagent under conditions wherein the diagnostic reagent will hybridize with h2520-59 nucleic acid molecules contained in said biological sample;

(c) detecting hybridization between h2520-59 nucleic acid molecules in the biological sample and the diagnostic reagent; and (d) comparing the level of hybridization between the biological sample and diagnostic reagent with the level of hybridization between a known concentration of h2520-59 nucleic acid molecules and the diagnostic reagent.

The invention also provides a method for detecting the presence of h2520-59 nucleic acid molecules in a tissue or cellular sample comprising the steps of:

(a) providing a tissue or cellular sample suspected of containing h2520-59 nucleic acid molecules;

(b) contacting the tissue or cellular sample with a diagnostic reagent under conditions wherein the diagnostic reagent will hybridize with h2520-59 nucleic acid molecules;

(c) detecting hybridization between h2520-59 nucleic acid molecules in the tissue or cellular sample and the diagnostic reagent; and (d) comparing the level of hybridization between the tissue or cellular sample and diagnostic reagent with the level of hybridization between a known concentration of h2520-59 nucleic acid molecules and the diagnostic reagent.

Interestingly, h2520-59 polypeptide was highly expressed in a wide range of primary human tumor cells. Therefore, the present polypeptide, and cognate nucleic acids, have demonstrated utility in distinguishing transformed cells from the non-transformed cellular background.

In another aspect of the present invention, the h2520-59 polypeptides may be used for identifying receptors or binding partners thereof ("h2520-59 receptors" or "h2520-59 binding partners"). Various forms of "expression cloning" have been extensively used to clone receptors for proteins or co-factors. See, for example, Simonsen et al., *Trends in Pharmacological Sciences,* 15: 437-441, 1994, and Tartaglia et al., *Cell,* 83:1263–1271, 1995. The isolation of the h2520-59 receptor(s) or h2520-59 binding partner(s) is useful for identifying or developing novel agonists and antagonists of the h2520-59 polypeptide-signaling pathway.

The present invention also provides for agonists and antagonists of h2520-59 polypeptide activity. Such agonists and antagonists include soluble h2520-59 ligand(s), anti-h2520-59 selective binding agents (such as h2520-59 antibodies and derivatives thereof), small molecules, peptides or peptide derivatives capable of binding h2520-59 polypeptides, or antisense oligonucleotides, any of which can be used for potentially treating one or more diseases or disorders, such as those recited herein;

In certain embodiments, a h2520-59 polypeptide agonist or antagonist may be a protein, peptide, carbohydrate, lipid, or small molecular weight molecule which interacts with a h2520-59 polypeptide to regulate its activity.

Also provided in the present invention is a polynucleotide described above attached to a solid support, as well as an array of polynucleotides comprising at least one polynucleotide as described above.

The h2520-59 polypeptides and nucleic acid molecules of the present invention may be used to treat, prevent, ameliorate, diagnose and/or detect diseases and disorders, including those recited herein. Expression analysis in biological, cellular or tissue samples suggests that h2520-59 polypeptide may play a role in the diagnosis and/or treatment of hyperproliferative diseases such as immune disorders, angiogenesis and vasculogenesis, wound healing, diabetes mellitus, psoriasis, liver disease, inflammation and cancer. This expression can de detected with a diagnostic agent such as a h2520-59 nucleic acid.

BRIEF DESCRIPTION OF THE FIGURES

FIGS. 1(a)–1(b) depicts a nucleic acid sequence (SEQ ID NO: 1) which encodes the human h2520-59 polypeptide sequence (SEQ ID NO: 2).

FIGS. 2(a)–2(c) present an alignment of the predicted amino acid sequence of the h2520-59 polypeptide (SEQ ID NO: 2) with the following polypeptide sequences: GENBANK BAB15597, Accession No: AK026945, (SEQ ID NO: 8), sequence number 1367 from WO 00/55350 (SEQ ID NO: 9), sequence number 1102 from WO 00/55350 (SEQ ID NO: 10), and JJ503-KS polypeptide (sequence number 9 from WO 00/08180; SEQ ID NO: 11) using the Pileup Program (Wisconsin GCC Program Package ver. 8.1).

DETAILED DESCRIPTION OF THE INVENTION

The section headings used herein are for organizational purposes only and are not to be construed as limiting the subject matter described therein. All references cited in this application are expressly incorporated by reference herein.

Definitions

The term "h2520-59 nucleic acid molecule" or "polynucleotide" refers to a nucleic acid molecule comprising or consisting of a nucleotide sequence set forth in SEQ ID NO: 1, a nucleotide sequence encoding the polypeptide set forth in SEQ ID NO: 2, or the nucleic acid sequence of the DNA insert in American Type Culture Collection (ATCC), 10801 University Boulevard, Manassas, Va. 20110-2209, deposit No. PTA-1759, deposited on Apr. 25, 2000, and nucleic acids molecules as defined herein.

The term "h2520-59 polypeptide" refers to a polypeptide comprising the amino acid sequence of SEQ ID NO: 2, and related polypeptides. Related polypeptides include: h2520-59 polypeptide allelic variants, h2520-59 polypeptide orthologs, h2520-59 polypeptide splice variants, h2520-59 polypeptide variants and h2520-59 polypeptide derivatives. The h2520-59 polypeptides may be mature polypeptides, as defined herein, and may or may not have an amino terminal methionine residue, depending on the method by which they are prepared.

The term "h2520-59 polypeptide allelic variant" refers to the polypeptide encoded by one of several possible naturally occurring alternate forms of a gene occupying a given locus on a chromosome of an organism or a population of organisms.

The term "h2520-59 polypeptide derivatives" refers to a polypeptide having an amino acid sequence as set forth in SEQ ID NO: 2, h2520-59 polypeptide allelic variants, h2520-59 polypeptide orthologs, h2520-59 polypeptide splice variants, or h2520-59 polypeptide variants, as defined herein, that have been chemically modified.

The term "h2520-59 polypeptide fragment" refers to a polypeptide that comprises a truncation at the amino terminus (with or without a leader sequence) and/or a truncation at the carboxy terminus of the polypeptide whose sequence is set forth in SEQ ID NO: 2, h2520-59 polypeptide allelic variants, h2520-59 polypeptide orthologs, h2520-59 polypeptide splice variants and/or a h2520-59 polypeptide variant having one or more amino acid additions or substitutions or internal deletions (wherein the resulting polypeptide is at least 6 amino acids or more in length) as compared to the h2520-59 polypeptide amino acid sequence set forth in SEQ ID NO: 2, h2520-59 polypeptide fragments may result from alternative RNA splicing or from in vivo protease activity. In preferred embodiments, truncations comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such h2520-59 polypeptide fragments may optionally comprise an amino terminal methionine residue. It will be appreciated that such fragments can be used, for example, to generate antibodies to h2520-59 polypeptides.

The term "h2520-59 fusion polypeptide" refers to a fusion of one or more amino acids (such as a heterologous peptide or polypeptide) at the amino or carboxy terminus of the polypeptide set forth in SEQ ID NO: 2, h2520-59 polypeptide allelic variants, h2520-59 polypeptide orthologs, h2520-59 polypeptide splice variants, or h2520-59 polypeptide variants having one or more amino acid deletions, substitutions or internal additions as compared to the h2520-59 polypeptide amino acid sequence set forth in SEQ ID NO: 2.

The term "h2520-59 polypeptide ortholog" refers to a polypeptide from another species that corresponds to the h2520-59 polypeptide amino acid sequence set forth in SEQ ID NO: 2. For example, mouse and human h2520-59 polypeptides are considered orthologs of each other.

The term "h2520-59 polypeptide splice variant" refers to a nucleic acid molecule, usually RNA, which is generated by alternative processing of intron sequences in an RNA primary transcript containing the non-contiguous coding region of the h2520-59 polypeptide amino acid sequence set forth in SEQ ID NO: 2.

The term "h2520-59 polypeptide variants" refers to h2520-59 polypeptides comprising amino acid sequences having one or more amino acid sequence substitutions, deletions (such as internal deletions and/or h2520-59 polypeptide fragments), and/or additions (such as internal additions and/or h2520-59 fusion polypeptides) as compared to the h2520-59 polypeptide amino acid sequence set forth in SEQ ID NO: 2 (with or without a leader sequence). Variants may be naturally occurring (e.g., h2520-59 polypeptide allelic variants, h2520-59 polypeptide orthologs and h2520-59 polypeptide splice variants) or may be artificially constructed. Such h2520-59 polypeptide variants may be prepared from the corresponding nucleic acid molecules having a DNA sequence that varies accordingly from the DNA sequence set forth in SEQ ID NO: 1. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "antigen" refers to a molecule or a portion of a molecule capable of being bound by a selective binding agent, such as an antibody, and additionally capable of being used in an animal to produce antibodies capable of binding to an epitope of each antigen. An antigen may have one or more epitopes.

The term "biologically active h2520-59 polypeptides" refers to h2520-59 polypeptides having at least one activity characteristic of the polypeptide comprising the amino acid sequence of SEQ ID NO: 2.

The terms "effective amount" and "therapeutically effective amount" each refer to the amount of a h2520-59 polypeptide or h2520-59 nucleic acid molecule used to support an observable level of one or more biological activities of the h2520-59 polypeptides set forth herein.

The term "expression vector" refers to a vector which is suitable for use in a host cell and contains nucleic acid sequences which direct and/or control the expression of heterologous nucleic acid sequences. Expression includes, but is not limited to, processes such as transcription, translation, and RNA splicing, if introns are present.

The term "host cell" is used to refer to a cell which has been transformed with a nucleic acid sequence and then of expressing a selected gene of interest. The term includes the progeny of the parent cell, whether or not the progeny is identical in morphology or in genetic make-up to the original parent, so long as the selected gene is present.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," refers to a measure of similarity which includes both identical matches and conservative substitution matches. If two polypeptide sequences have, for example, 10/20 identical amino acids, and the remainder are all non-conservative substitutions, then the percent identity and similarity would both be 50%. If, in the same example, there are five more positions where there are conservative substitutions, then the percent identity remains 50%, but the percent similarity would be 75% (15/20). Therefore, in cases where there are conservative substitutions, the degree of percent similarity between two polypeptides will be higher than the percent identity between those two polypeptides.

The term "isolated nucleic acid molecule" refers to a nucleic acid molecule of the invention that (1) has been separated from at least about 50 percent of proteins, lipids, carbohydrates or other materials with which it is naturally found when total DNA is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "isolated polypeptide" refers to a polypeptide of the present invention that (1) has been separated from at least about 50 percent of polynucleotides, lipids, carbohydrates or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "mature h2520-59 polypeptide" refers to a h2520-59 polypeptide lacking a leader sequence. A mature h2520-59 polypeptide may also include other modifications such as proteolytic processing of the amino terminus (with or without a leader sequence) and/or the carboxy terminus, cleavage of a smaller polypeptide from a larger precursor, N-linked and/or O-linked glycosylation, and the like. An exemplary mature h2520-59 polypeptide is depicted by amino acid residue 1 through amino acid residue 358 of SEQ ID NO: 2.

The terms "nucleic acid sequence" or "nucleic acid molecule" refer to a DNA or RNA sequence. The terms encompass molecules formed from any of the known base analogs of DNA and RNA such as, but not limited to, 4-acetylcytosine, 8-hydroxy-N-6-methyladenine, aziridinylcytosine, pseudoisocytosine, 5-(carboxyhydroxlmethyl) uracil, 5-fluorouracil, 5-bromouracil, 5-carboxymethylaminomethyl-2-thiouracil, 5-carboxymethylaminomethyluracil, dihydrouracil, inosine, N6 isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, 2-thiocytosine, and 2,6-diaminopurine.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "operably linked" is used herein to refer to a method of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably linked" to the coding sequence.

The terms "pharmaceutically acceptable carrier" or "physiologically acceptable carrier" as used herein refer to one or more formulation materials suitable for accomplishing or enhancing the delivery of the h2520-59 polypeptide, h2520-59 nucleic acids molecule, or h2520-59 selective binding agent as a pharmaceutical composition.

The term "selective binding agent" refers to a molecule or molecules having specificity for a h2520-59 polypeptide. As used herein the terms "specific" and "specifically" refer to the ability of the selective binding agents to bind to human h2520-59 polypeptides and not to bind to human non-h2520-59 polypeptides. It will be appreciated, however, that the selective binding agents may also bind orthologs of the polypeptide set forth in SEQ ID NO: 2, that is, interspecies versions thereof, such as mouse and rat polypeptides.

The term "transduction" is used to refer to the transfer of nucleic acid from one bacterium to another. "Transduction" also refers to the acquisition and transfer of eukaryotic cellular sequences by viruses such as retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, for example, Graham et al., *Virology*, 52: 456, 1973; Sambrook et al., *Molecular Cloning, A Laboratory Manual*, Cold Spring Harbor Laboratories (New York, 1989); Davis et al, *Basic Methods in Molecular Biology*, Elsevier, 1986; and Chu et al., *Gene*, 13:197, 1981. Such techniques can be used to introduce one or more exogenous DNA moieties into suitable host cells.

The term "transformation" as used herein refers to a change in a cell's genetic characteristics, and a cell has been transformed when it has been modified to contain new DNA. For example, a cell is transformed where it is genetically modified from its native state. Following transfection or transduction, the transforming DNA may recombine with that of the cell by physically integrating into a chromosome of the cell, it may be maintained transiently as an episomal element without being replicated, or it may replicate independently as a plasmid. A cell is considered to have been stably transformed when the DNA is replicated with the division of the cell.

The term "vector" is used to refer to any molecule (e.g., nucleic acid, plasmid, or virus) used to transfer coding information to a host cell.

Relatedness of Nucleic Acid Molecules and/or Polypeptides

It is understood that related nucleic acid molecules include allelic or splice variants of the nucleic acid molecule of SEQ ID NO: 1, and include sequences which are complementary to any of the above nucleotide sequences. Related nucleic acid molecules also include a nucleotide sequence encoding a polypeptide comprising or consisting essentially of a substitution, modification, addition and/or deletion of one or more amino acid residues compared to the polypeptide in SEQ ID NO: 2.

Fragments include molecules which encode a polypeptide of at least about 25 amino acid residues, or about 50, or about 75, or about 100, or greater than about 100 amino acid residues of the polypeptide of SEQ ID NO: 2.

In addition, related h2520-59 nucleic acid molecules include those molecules which comprise nucleotide sequences which hybridize under moderately or highly stringent conditions as defined herein with the fully complementary sequence of the nucleic acid molecule of SEQ ID NO: 1, or of a molecule encoding a polypeptide, which polypeptide comprises the amino acid sequence as shown in SEQ ID NO: 2, or of a nucleic acid fragment as defined herein, or of a nucleic acid fragment encoding a polypeptide as defined herein. Hybridization probes may be prepared using the h2520-59 sequences provided herein to screen cDNA, genomic or synthetic DNA libraries for related sequences. Regions of the DNA and/or amino acid sequence of a h2520-59 polypeptide that exhibit significant identity to known sequences are readily determined using sequence alignment algorithms as described herein and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride and 0.0015 M sodium citrate at 65–68° C.; or 0.015 M sodium chloride, 0.0015 M sodium citrate, and 50% formamide at 42° C. See Sambrook et al., *Molecular Cloning: A Laboratory Manual*, 2$^{nd}$ Ed, Cold Spring Harbor Laboratory, (Cold Spring Harbor, N.Y. (1989) and Anderson et al., *Nucleic Acid Hybridization: a Practical Approach*, Ch. 4, IRL Press Limited (Oxford, England).

More stringent conditions (such as higher temperature, lower ionic strength, higher formamide, or other denaturing agent) may also be used; however, the degree of hybridization will be affected. Other agents may be included in the hybridization and washing buffers for the purpose of reducing non-specific and/or background hybridization. Examples are 0.1% bovine serum albumin, 0.1% polyvinylpyrrolidone, 0.1% sodium pyrophosphate, 0.1% sodium dodecylsulfate (NaDodSO$_4$ or SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8–7.4; however, at typical ionic strength conditions, the rate of hybridization is nearly independent of pH. (See Anderson et al., *Nucleic Acid Hybridization: a Practical Approach*, Ch. 4, IRL Press Limited (Oxford, England)).

Factors affecting the stability of DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(° C.)=81.5+16.6(\log[Na-])+0.41(\% G+C)-600/N-0.72(\%\text{formamide})$$

where N is the length of the duplex formed in nucleotides, [Na$^+$] is the molar concentration of the sodium ion in the hybridization or washing solution, and % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride and 0.0015 M sodium citrate at 50–65° C.; or 0.015 M sodium chloride, 0.0015 M sodium citrate, and 20% formamide at 37–50° C. By way of example, a "moderately stringent" condition of 50° C. in 0.015 M sodium ion will allow about a 21% mismatch.

It will be appreciated by those skilled in the art that there is no absolute distinction between "highly" and "moderately" stringent conditions. For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1.0 M NaCl* for oligonucleotide probes up to about 20 nucleotides is given by:

$$Tm=2° C. \text{ per } A-T \text{ base pair}+4° C. \text{ per } G-C \text{ base pair}$$

*The sodium ion concentration in 6× salt sodium citrate (SSC) is 1.0 M. See Suggs et al., *Developmental Biology Using Purified Genes*, p. 683, Brown and Fox (eds.) (1981).

High stringency washing conditions for oligonucleotides are usually at a temperature of 0–5° C. below the Tm of the oligonucleotide in 6×SSC, 0.1% SDS for longer oligonucleotides.

In another embodiment, related nucleic acid molecules comprise or consist of a nucleotide sequence that is about 70 percent (70%) identical to the nucleotide sequence as shown in SEQ ID NO: 1, or comprise or consist essentially of a nucleotide sequence encoding a polypeptide that is about 70 percent (70%) identical to the polypeptide set forth in SEQ ID NO: 2. In preferred embodiments, the nucleotide sequences are about 75 percent, or about 80 percent, or about 85 percent, or about 90 percent, or about 95, 96, 97, 98, or 99 percent identical to the nucleotide sequence as shown in SEQ ID NO: 1, or the nucleotide sequences encode a polypeptide that is about 75 percent, or about 80 percent, or about 85 percent, or about 90 percent, or about 95, 96, 97, 98, or 99 percent identical to the polypeptide sequence set forth in SEQ ID NO: 2.

Differences in the nucleic acid sequence may result in conservative and/or non-conservative modifications of the amino acid sequence relative to the amino acid sequence of SEQ ID NO: 2.

Conservative modifications to the amino acid sequence of SEQ ID NO: 2 (and the corresponding modifications to the encoding nucleotides) will produce h2520-59 polypeptides having functional and chemical characteristics similar to those of a naturally occurring h2520-59 polypeptide. In contrast, substantial modifications in the functional and/or chemical characteristics of h2520-59 polypeptides may be accomplished by selecting substitutions in the amino acid sequence of SEQ ID NO: 2 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described (Cunningham and Wells, Science 244:1081–1085, 1989) for "alanine scanning mutagenesis".

Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties.

Naturally occurring residues may be divided into classes based on common side chain properties:

1) hydrophobic: norleucine, Met, Ala, Val, Leu, He;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human h2520-59 polypeptide that are homologous, or similar, with non-human h2520-59 polypeptide orthologs, or into the non-homologous regions of the molecule.

In making such changes, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); typtophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157: 105–131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended, in part, for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the h2520-59 polypeptide, or to increase or decrease the affinity of the h2520-59 polypeptides for their substrates, described herein.

Exemplary amino acid substitutions are set forth in Table I.

TABLE I

Conservative Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide set forth in SEQ ID NO: 2 using well known techniques. For identifying suitable areas of the molecule that may be changed without destroying activity, one skilled in the art may target areas not likely to be important for activity. For example, when similar polypeptides with similar activities from the same species or from other species are known, one skilled in the art may compare the amino acid sequence of a h2520-59 polypeptide to such similar polypeptides. With such a comparison, one can identify residues and portions of the molecules that are conserved among similar polypeptides. It will be appreciated that changes in areas of a h2520-59 polypeptide that are not conserved relative to such similar polypeptides would be less likely to adversely affect the biological activity and/or structure of the h2520-59 polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a h2520-59 polypeptide that correspond to amino acid residues which are important for activity or structure in similar polypeptides. One skilled in the art may opt for chemically similar amino acid substitutions for such predicted important amino acid residues of h2520-59 polypeptides.

One skilled in the art can also analyze the three-dimensional structure and amino acid sequence in relation to that structure in similar polypeptides. In view of such information, one skilled in the art may predict the alignment of amino acid residues of a h2520-59 polypeptide with respect to its three-dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided, either alone or in combination with other mutations.

The h2520-59 polypeptide analogs of the invention can be determined by comparing the amino acid sequence of h2520-59 polypeptide with related family members. Exemplary h2520-59 polypeptide-related family members may include, but are not limited to, GENBANK BAB 15597, Accession No. BAB 15597 (SEQ ID NO: 8), sequence number 1367 in WO 00/55350 (SEQ ID NO: 9), sequence number 1102 in WO 00/55350 (SEQ ID NO: 10), and JJ503-KS polypeptide (sequence number 9 in WO 00/08180; SEQ ID NO: 11). This comparison can be accomplished by using a Pileup alignment (Wisconsin GCG Program Package, ver. 8.1; as shown in FIG. 2) or an equivalent (overlapping) comparison with multiple family members within conserved and non-conserved regions. As shown in FIG. 2, the predicted amino acid sequence of a h2520-59 polypeptide (SEQ ID NO: 2) is aligned with SEQ ID NO: 8, SEQ ID NO: 9, SEQ ID NO: 10, and SEQ ID NO: 11. The public sequence, GENBANK BAB15597, Accession No. AK026945 (SEQ ID NO: 8), was entered in GENBANK on Sep. 29, 2000 with no function described, but is 100% aligned with h2520-59 (SEQ ID NO: 2). The other sequences displayed in FIG. 2 (SEQ ID NO: 9–11) are partially aligned with h2520-59 (SEQ ID NO: 2).

Other h2520-59 polypeptide analogs can be identified using these or other methods known to those of skill in the art. These overlapping sequences provide guidance for conservative and non-conservative amino acids substitutions resulting in additional h2520-59 analogs. It will be appreciated that these amino acid substitutions can consist of naturally occurring or non-naturally occurring amino acids. For example, as depicted in FIG. 2, alignment of the amino acids of these related polypeptides indicates potential h2520-59 analogs may have the Val residue at position 31 of SEQ ID NO: 2 substituted with an Ile, Met, Leu, Phe, Ala, or norleucine residue; the Thr residue at position 60 of SEQ ID NO: 2 substituted with a Ser residue; the Glu residue at position 229 of SEQ ID NO: 2 substituted with an Asp residue; the His residue at position 258 of SEQ ID NO: 2 substituted with an Asn, Gln, Lys, or Arg residue; the Gly residue at position 283 of SEQ ID NO: 2 substituted with a Pro or Ala residue; and the Trp residue at position 314 of SEQ ID NO: 2 substituted with a Tyr or Phe residue.

A number of scientific publications have been devoted to the prediction of secondary structure. See Chou et al., *Biochemistry*, 13(2): 222–245, 1974; Chou et al., *Biochemistry*, 113(2): 211–222, 1974; Chou et al., *Adv. Enzymol. Relat. Areas Mol. Biol.*, 47:45–148, 1978; Chou et al., *Ann. Rev. Biochem.*, 47: 251–276 and Chou et al., *Biophys. J.*, 26: 367–384, 1979. Moreover, computer programs are currently available to assist with predicting secondary structure. One method of predicting secondary structure is based upon homology modeling. For example, two polypeptides or proteins which have a sequence identity of greater than 30%, or similarity greater than 40%, often have similar structural topologies. The recent growth of the protein structural database (PDB) has provided enhanced predictability of secondary structure, including the potential number of folds within a polypeptide's or protein's structure. See Holm et al., *Nucl. Acid. Res.*, 27(1):244–247, 1999. It has been suggested (Brenner et al., *Curr. Opin. Struct. Biol.*, 7(3):369–376, 1997) that there are a limited number of folds in a given polypeptide or protein and that once a critical number of structures have been resolved, structural prediction becomes dramatically more accurate.

Additional methods of predicting secondary structure include "threading" (Jones et al., *Current Opin. Struct. Biol.*, 7(3):377–87 (1997); Sippl et al., *Structure*, 4(1):15–9 (1996)), "profile analysis" (Bowie et al., *Science*, 253:164–170 (1991); Gribskov et al., *Meth. Enzym.*, 183:146–159 (1990); Gribskov et al., *Proc. Nat. Acad. Sci.*, 84(13):4355–4358 (1987)), and "evolutionary linkage" (See Home, supra, and Brenner, supra 1997).

Preferred h2520-59 polypeptide variants include glycosylation variants wherein the number and/or type of glycosylation sites has been altered compared to the amino acid sequence set forth in SEQ ID NO: 2. In one embodiment, h2520-59 polypeptide variants comprise a greater or a lesser number of N-linked glycosylation sites than the amino acid sequence set forth in SEQ ID NO: 2. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-inked carbohydrate chains wherein one or more N-linked glycosylation sites (typically those that are naturally occurring) are eliminated and one or more new N-linked sites are created. Additional preferred h2520-59-like variants include cysteine variants, wherein one or more cysteine residues are deleted from or substituted for another amino acid (e.g., serine) as compared to the amino acid sequence set forth in SEQ ID NO: 2. Cysteine variants are useful when h2520-59 polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In addition, the polypeptide comprising the amino acid sequence of SEQ ID NO: 2 or a h2520-59 polypeptide variant may be fused to a homologous polypeptide to form a homodimer or to a heterologous polypeptide to form a heterodimer. Heterologous peptides and polypeptides include, but are not limited to: an epitope to allow for the detection and/or isolation of a h2520-59 fusion polypeptide; a transmembrane receptor protein or a portion thereof, such as an extracellular domain, or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence set forth in SEQ ID NO: 2 or a h2520-59 polypeptide variant.

Fusions can be made either at the amino terminus or at the carboxy terminus of the polypeptide comprising the amino acid sequence set forth in SEQ ID NO: 2 or a h2520-59 polypeptide variant. Fusions may be direct with no linker or adapter molecule or indirect using a linker or adapter molecule. A linker or adapter molecule may be one or more amino acid residues, typically from 20 to about 50 amino acid residues. A linker or adapter molecule may also be designed with a cleavage site for a DNA restriction endonuclease in an encoding polynucleotide or for a protease to allow for the separation of the fused moieties. It will be appreciated that once constructed, the fusion polypeptides can be derivatized according to the methods described herein.

In a further embodiment of the invention, the polypeptide comprising the amino acid sequence of SEQ ID NO: 2 or a h2520-59 polypeptide variant is fused to one or more domains of an Fc region of human IgG. Antibodies comprise two functionally independent parts, a variable domain known as "Fab," which binds antigens, and a constant domain known as "Fc," which is involved in effector functions such as complement activation and attack by phagocytic cells. An Fc has a long serum half-life, whereas an Fab is short-lived. Capon et al., *Nature*, 337: 525–31 (1989). When constructed together with a therapeutic protein, an Fc domain can provide longer half-life or incorporate such functions as Fc receptor binding, protein A binding, complement fixation and perhaps even placental transfer. Id. Table II summarizes the use of certain Fc fusions known in the art.

TABLE II

Fc Fusion with Therapeutic Proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al., J. Immunol., 154: 5590–600, 1995 |
| IgG1 | TNF receptor | septic shock | Fisher et al., N. Engl. J. Med., 334: 1697–1702, 1996; Van Zee et al., J. Immunol., 156: 2221–30, 1996 |
| IgG, IgA, IgM, or IgE (excluding the first domain) | TNF receptor | inflammation, autoimmune disorders | U.S. Pat. 5,808,029 |
| IgG1 | CD4 receptor | AIDS | Capon et al., Nature, 337: 525–31, 1989 |
| IgG1, IgG3 | N-terminus of IL-2 | anti-cancer, antiviral | Harvill et al., Immunotech., 1: 95–105, 1995 |
| IgG1 | C-terminus of OPG | osteoarthritis; bone density | WO 97/23614, published Jul. 3, 1997 |
| IgG1 | N-terminus of leptin | anti-obesity | PCT/US 97/23183, filed Dec. 11, 1997 |
| Human Ig Cγ1 | CTLA-4 | autoimmune disorders | Linsley, J. Exp. Med., 174: 561–9, 1991 |

In one example, all or a portion of the human IgG hinge, CH2 and CH3 regions may be fused at either the N-terminus or C-terminus of the h2520-59 polypeptides using methods known to the skilled artisan. The resulting h2520-59 fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, reduce aggregation, etc.

Identity and similarity of related nucleic acid molecules and polypeptides can be readily calculated by known methods. Such methods include, but are not limited to, those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; *Sequence Analysis Primer*, Gribskov, M. and Devereux, J., eds., M. Stockton Press, New York, 1991; and Carillo et al., *SIAM J., Applied Math.,* 48:1073, 1988.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., *Nucl. Acids. Res.,* 12:387, 1984; Genetics Computer Group, University of Wisconsin, Madison, Wis.), BLASTP, BLASTN, and FASTA (Altschul et al., *J. Mol.*

*Biol.*, 215:403–410, 1990)). The BLASTX program is publicly available from the National Center for Biotechnology Information (NCBI) and other sources (BLAST Manual, Altschul et al. *NCB/NLM/NIH Bethesda, Md.* 20894; Altschul et al., supra). The well-known Smith-Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in a preferred embodiment, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. A standard comparison matrix (see Dayhoff et al., *Atlas of protein Sequence and Structure*, vol. 5, supp.3 (1978) for the PAM 250 comparison matrix; Henikoff et al., *Proc. Natl. Acad. Sci USA,* 89:10915–10919 (1992) for the BLOSUM 62 comparison matrix) is also used by the algorithm.

Preferred parameters for a polypeptide sequence comparison include the following:

Algorithm: Needleman et al., *J. Mol. Biol.*, 48, 443–453, 1970;

Comparison matrix: BLOSUM 62 from Henikoff et al., Proc. Natl.

Acad. Sci. USA, 89: 10915–10919, 1992);

Gap Penalty: 12

Gap Length Penalty: 4

Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparisons include the following:

Algorithm: Needleman et al., *J. Mol. Biol.*, 48: 443–453, 1970;

Comparison matrix: matches=+10, mismatch=0

Gap Penalty: 50

Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used by those of skill in the art, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA, and additionally, whether the comparison is between given pairs of sequences (in which case GAP or BestFit are generally preferred) or between one sequence and a large database of sequences (in which case FASTA or BLASTA are preferred).

Synthesis

It will be appreciated by those skilled in the art that the nucleic acid and polypeptide molecules described herein may be produced by recombinant and other means.

Nucleic Acid Molecules

The nucleic acid molecules encode a polypeptide comprising the amino acid sequence of a h2520-59 polypeptide and can readily be obtained in a variety of ways including, without limitation, chemical synthesis, cDNA or genomic library screening, expression library screening and/or PCR amplification of cDNA.

Recombinant DNA methods used herein are generally those set forth in Sambrook et al., *Molecular Cloning: A Laboratory Manual*, Cold Spring Harbor Laboratory Press, Cold Spring Harbor, N.Y. (1989), and/or Ausubel et al., eds., *Current Protocols in Molecular Biology*, Green Publishers Inc. and Wiley and Sons, NY (1994). The present invention provides for nucleic acid molecules as described herein and methods for obtaining such molecules.

Where a gene encoding the amino acid sequence of a h2520-59 polypeptide has been identified from one species, all or a portion of that gene may be used as a probe to identify orthologs or related genes from the same species. The probes or primers may be used to screen cDNA libraries from various tissue sources believed to express the h2520-59 polypeptide. In addition, part or all of a nucleic acid molecule having the sequence set forth in SEQ ID NO: 1 may be used to screen a genomic library to identify and isolate a gene encoding the amino acid sequence of a h2520-59 polypeptide. Typically, conditions of moderate or high stringency will be employed for screening to minimize the number of false positives obtained from the screening.

Nucleic acid molecules encoding the amino acid sequence of h2520-59 polypeptides may also be identified by expression cloning which employs the detection of positive clones based upon a property of the expressed protein. Typically, nucleic acid libraries are screened by the binding of an antibody or other binding partner (e.g., receptor, ligand, or co-factor) to cloned proteins which are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence which encodes the amino acid sequence of a h2520-59 polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of a h2520-59 polypeptide can be inserted into an expression vector. By introducing the expression vector into an appropriate host, the encoded h2520-59 polypeptide may be produced in large amounts.

Another method for obtaining a suitable nucleic acid sequence is the polymerase chain reaction (PCR). In this method, cDNA is prepared from poly(A)+RNA or total RNA using the enzyme reverse transcriptase. Two oligonucleotide primers, typically complementary to two separate regions of cDNA encoding the amino acid sequence of a h2520-59 polypeptide, are then added to the cDNA along with a polymerase such as Taq polymerase, and the polymerase amplifies the cDNA region between the two primers.

Another means of preparing a nucleic acid molecule encoding the amino acid sequence of a h2520-59 polypeptide is chemical synthesis using methods well known to the skilled artisan such as those described by Engels et al, (*Angew. Chem. Intl. Ed.*, 28: 716–734, 1989). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of a h2520-59 polypeptide will be several hundred nucleotides in length. Nucleic acids larger than about 100 nucleotides can be synthesized as several fragments using these methods. The fragments can then be ligated together to form the full-length nucleotide sequence of a h2520-59 polypeptide. Usually, the DNA fragment encoding the amino terminus of the polypeptide will have an ATG, which encodes a methionine residue. This methionine may or may not be present on the mature form of the h2520-59 polypeptide, depending on whether the polypeptide produced in the host cell is designed to be secreted from that cell. Other methods known to the skilled artisan may be used as well.

In certain embodiments, nucleic acid variants contain codons which have been altered for the optimal expression of a h2520-59 polypeptide in a given host cell. Particular codon alterations will depend upon the h2520-59 polypeptide(s) and host cell(s) selected for expression. Such "codon optimization" can be carried out by a variety of methods, for example, by selecting codons which are preferred for use in highly expressed genes in a given host cell. Computer algorithms which incorporate codon frequency tables such as "Ecohigh.cod" for codon preference of highly expressed bacterial genes may be used and are provided by the University of Wisconsin Package Version 9.0, Genetics Computer Group, Madison, Wis. Other useful codon frequency tables include "Celegans_high.cod," "Celegans_low.cod," "Drosophila_high.cod," "Human_high.cod," "Maize_high.cod," and "Yeast_high.cod."

Vectors and Host Cells

A nucleic acid molecule encoding the amino acid sequences of h2520-59 polypeptide may be inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of h2520-59 polypeptide may be amplified/expressed in prokaryotic, yeast, insect (baculovirus systems), and/or eukaryotic host cells. Selection of the host cell will depend in part on whether a h2520-59 polypeptide is to be post-translationally modified (e.g., glycosylated and/or phosphorylated). If so, yeast, insect, or mammalian host cells are preferable. For a review of expression vectors, see *Meth. Enz.*, v.185, D. V. Goeddel, ed. Academic Press Inc., San Diego, Calif. (1990).

Typically, expression vectors used in any of the host cells will contain sequences for plasmid maintenance and for cloning and expression of exogenous nucleotide sequences. Such sequences, collectively referred to as "flanking sequences" in certain embodiments, will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the h2520-59 polypeptide coding sequence; the oligonucleotide sequence encodes polyHis (such as hexaHis), or another "tag" such as FLAG, HA (hemaglutinin influenza virus) or myc for which commercially available antibodies exist. This tag is typically fused to the polypeptide upon expression of the polypeptide, and can serve as a means for affinity purification of the h2520-59 polypeptide from the host cell. Affinity purification can be accomplished, for example, by column chromatography using antibodies against the tag as an affinity matrix. Optionally, the tag can subsequently be removed from the purified h2520-59 polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences which normally function to regulate h2520-59 polypeptide expression. As such, the source of a flanking sequence may be any prokaryotic or eukaryotic organism, any vertebrate or invertebrate organism, or any plant, provided that the flanking sequences is in, and can be activated by, the host cell machinery.

The flanking sequences useful in the vectors of this invention may be obtained by any of several methods well known in the art. Typically, flanking sequences useful herein other than the endogenous h2520-59 gene flanking sequences will have been previously identified by mapping and/or by restriction endonuclease digestion and can thus be isolated from the proper tissue source using the appropriate restriction endonucleases. In some cases, the full nucleotide sequence of one or more flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with suitable oligonucleotide and/or flanking sequence fragments from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically apart of those prokaryotic expression vectors purchased commercially, and the origin aids in the amplification of the vector in a host cell. Amplification of the vector to a certain copy number can, in some cases, be important for the optimal expression of the h2520-59 polypeptide. If the vector of choice does not contain an origin of replication site, one may be chemically synthesized based on a known sequence, and ligated into the vector. For example, the origin of replication from the plasmid pBR322 (Product No. 303-3s, New England Biolabs, Beverly, Mass.) is suitable for most gram-negative bacteria and various origins (e.g., SV40, polyoma, adenovirus, vesicular stomatitus virus (VSV) or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene which will be expressed. Amplification is the process wherein genes which are in greater demand for the production of a protein critical for growth are reiterated within the chromosome(s) of successive generations of recombinant cells. Examples of suitable selectable markers for mammalian cells include dihydrofolate reductase (DHFR) and thymidine kinase. The mammalian cell transformants are placed under selection pressure which only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes h2520-59 polypeptide. As a result, increased quantities of h2520-59 polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the h2520-59 polypeptide to be expressed. The Shine-Dalgarno sequence is varied but is typically a polypurine (ie., having a high A-G content). Many Shine-Dalgarno sequences have been identified, each of which can be readily synthesized using methods set forth herein and used in a prokaryotic vector.

A leader, or signal, sequence may be used to direct a h2520-59 polypeptide out of the host cell. Typically, a nucleotide sequence encoding the signal sequence is positioned in the coding region of the h2520-59 nucleic acid molecule, or directly at the 5' end of the h2520-59 polypeptide coding region. Many signal sequences have been identified, and any of those that are functional in the selected host cell may be used in conjunction with the h2520-59 nucleic acid molecule. Therefore, a signal sequence may be homologous (naturally occurring) or heterologous to the h2520-59 gene or cDNA. Additionally, a signal sequence may be chemically synthesized using methods described herein. In most cases, the secretion of a h2520-59 polypeptide from the host cell via the presence of a signal peptide will result in the removal of the signal peptide from the secreted h2520-59 polypeptide. The signal sequence may be a component of the vector, or it may be a part of a h2520-59 nucleic acid molecule that is inserted into the vector.

Included within the scope of this invention is the use of either a nucleotide sequence encoding a native h2520-59 polypeptide signal sequence joined to a h2520-59 polypeptide coding region or a nucleotide sequence encoding a heterologous signal sequence joined to a h2520-59 polypeptide coding region. The heterologous signal sequence selected should be one that is recognized and processed, i.e., cleaved by a signal peptidase, by the host cell. For prokaryotic host cells that do not recognize and process the native h2520-59 signal sequence, the signal sequence is substituted by a prokaryotic signal sequence selected, for example, from the group of the alkaline phosphatase, penicillinase, or heat-stable enterotoxin II leaders. For yeast secretion, the native h2520-59 polypeptide signal sequence may be substituted by the yeast invertase, alpha factor, or acid phosphatase leaders. In mammalian cell expression the native signal sequence is satisfactory, although other mammalian signal sequences may be used.

In some cases, such as where glycosylation is desired in a eukaryotic host cell expression system, one may manipulate the various presequences to improve glycosylation or yield. For example, one may alter the peptidase cleavage site of a particular signal peptide, or add presequences, which also may affect glycosylation. The final protein product may have, in the −1 position (relative to the first amino acid of the mature protein), one or more additional amino acids incident to expression, which may not have been totally removed. For example, the final protein product may have one or two amino acid residues found in the peptidase cleavage site, attached to the N-terminus. Alternatively, use of some enzyme cleavage sites may result in a slightly truncated form of the desired h2520-59 polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the h2520-59 gene, especially where the gene used is a full-length genomic sequence or a fragment thereof. Where the intron is not naturally occurring within the coding region (as for most cDNAs), the intron(s) may be obtained from another source. The position of the intron with respect to flanking sequences and the h2520-59 gene is generally important, as the intron must be transcribed to be effective. Thus, when a h2520-59 cDNA molecule is being transcribed, the preferred position for the intron is 3' to the transcription start site, and 5' to the polyA transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

The expression and cloning vectors of the present invention will each typically contain a promoter that is recognized by the host organism and operably linked to the molecule encoding a h2520-59 polypeptide. Promoters are untranscribed sequences typically located upstream (5') to the start codon of a structural gene (generally within about 100 to 1000 bp) that control the transcription of the structural gene. Promoters are conventionally grouped into one of two classes, inducible promoters and constitutive promoters. In this context, inducible promoters include repressible/derepressible promoters and conventional inducible promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding a h2520-59 polypeptide by, e.g., removing the promoter from the source DNA by restriction enzyme digestion and inserting the desired promoter sequence into the vector. The native h2520-59 promoter sequence may be used to direct amplification and/or expression of a h2520-59 nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their sequences have been published, thereby enabling one skilled in the art to ligate them to the desired DNA sequence(s), using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowl pox virus, adenovirus (such as Adenovirus 2), bovine papilloma virus, avian sarcoma virus, cytomegalovirus (CMV), a retrovirus, hepatitis-B virus and most preferably Simian Virus 40 (SV40). Other suitable mammalian promoters include heterologous mammalian promoters, e.g., heat-shock promoters and the actin promoter.

Additional promoters which may be of interest in controlling h2520-59 gene transcription include, but are not limited to: the SV40 early promoter region (Benoist and Chambon, *Nature,* 290: 304–310, 1981); the CMV promoter; the promoter contained in the 3' long terminal repeat of Rous sarcoma virus (Yamamoto et al., *Cell,* 22: 787–797, 1980); the herpes simplex thymidine kinase promoter (Wagner et al., *Proc. Natl. Acad. Sci. USA,* 78: 144–1445, 1981); the regulatory sequences of the metallothionein gene (Brinster et al., *Nature,* 296: 39–42, 1982); prokaryotic expression vectors such as the beta-lactamase promoter (Villa-Kamaroff, et al., *Proc. Natl. Acad. Sci. USA,* 75: 3727–3731, 1978); or the tac promoter (DeBoer, et al., *Proc. Natl. Acad. Sci. USA,* 80: 21–25, 1983). Also of interest are the following animal transcriptional control regions, which exhibit tissue specificity and have been utilized in transgenic animals: the elastase I gene control region, which is active in pancreatic acinar cells (Swift et al., *Cell,* 38: 639–646, 1984; Ornitz et al., *Cold Spring Harbor Synzp. Quant. Biol.,* 50: 399–409, 1986; MacDonald, *Hepatology,* 7: 425–515, 1987); the insulin gene control region, which is active in pancreatic beta cells (Hanahan, *Nature,* 315: 115–122, 1985); the immunoglobulin gene control region, which is active in lymphoid cells (Grosschedl et al., *Cell,* 38: 647–658 (1984); Adames et al., *Nature,* 318: 533–538 (1985); Alexander et al., *Mol. Cell. Biol.,* 7: 1436–1444, 1987); the mouse mammary tumor virus control region, which is active in testicular, breast, lymphoid and mast cells (Leder et al., *Cell,* 45: 485–495, 1986); the albumin gene control region, which is active in liver (Pinkert et al., *Genes and Devel,* 1: 268–276, 1987); the alphafetoprotein gene control region, which is active in liver (Krumlauf et al., *Mol. Cell. Biol.,* 5: 1639–1648, 1985; Hammer et al., *Science,* 235: 53–58, 1987); the alpha 1-antitrypsin gene control region, which is active in the liver (Kelsey et al., *Genes and Devel,* 1: 161–171, 1987); the beta-globin gene control region, which is active in myeloid cells (Mogram et al., *Nature,* 315: 338–340, 1985; Kollias et al., *Cell,* 46: 89–94, 1986); the myelin basic protein gene control region, which is active in oligodendrocyte cells in the brain (Readhead et al., *Cell,* 48: 703–712, 1987); the myosin light chain-2 gene control region which is active in skeletal muscle (Sani, *Nature,* 314: 283–286, 1985); and the gonadotropic releasing hormone gene control region, which is active in the hypothalamus (Mason et al., *Science,* 234: 1372–1378, 1986).

An enhancer sequence may be inserted into the vector to increase the transcription of a DNA encoding a h2520-59 polypeptide of the present invention by higher eukaryotes. Enhancers are cis-acting elements of DNA, usually about 10–300 bp in length, that act on the promoter to increase its transcription. Enhancers are relatively orientation- and position-independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a h2520-59 nucleic acid molecule, it is typically located at a site 5' from the promoter.

Expression vectors of the invention may be constructed from a starting vector such as a commercially available vector. Such vectors may or may not contain all of the desired flanking sequences. Where one or more of the desired flanking sequences are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen Company, Carlsbad, Calif.), pBSII (Stratagene Company, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII; Invitrogen), pDSR-alpha (PCT Publication No. WO90/14363) and pFastBacDual (Gibco/BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast, or virus vectors such as a baculovirus expression system (pBacPAK plasmid derivatives, Clontech, Palo Alto, Calif.).

After the vector has been constructed and a nucleic acid molecule encoding a h2520-59 polypeptide has been inserted into the proper site of the vector, the completed vector may be inserted into a suitable host cell for amplification and/or polypeptide expression. The transformation of an expression vector for a h2520-59 polypeptide into a selected host cell may be accomplished by well-known methods such as transfection, infection, calcium chloride-mediated transformation, electroporation, microinjection, lipofection or the DEAE-dextran method or other known techniques. The method selected will in part be a function of the type of host cell to be used. These methods and other suitable methods are well-known to the skilled artisan and are set forth, for example, in Sanbrook et al., supra.

Host cells may be prokaryotic host cells (such as *E. coli*) or eukaryotic host cells (such as yeast, insect, or vertebrate cells). The host cell, when cultured under appropriate conditions, may synthesize a h2520-59 polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity, such as glycosylation or phosphorylation, and ease of folding into a biologically active molecule.

A number of suitable host cells are known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61); CHO DHFR-cells (Urlaub et al., *Proc. Natl. Acad. Sci. USA*, 97: 4216–4220, 1980; ATCC No. CRL9096), human embryonic kidney (HEK) 293 or 293T cells (ATCC No. CRL1573); or 3T3 cells (ATCC No. CCL92). The selection of suitable mammalian host cells and methods for transformation, culture, amplification, screening, product production and purification are known in the art. Other suitable mammalian cell lines are the monkey COS-1 (ATCC No. CRL1650) and COS-7 (ATCC No. CRL1651) cell lines and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include, but are not limited to, mouse neuroblastoma N2A cells, HeLa, mouse L-929 cells, 3T3 lines derived from Swiss, Balb-c or NIH mice, BHK or HaK hamster cell lines, which are also available from the ATCC. Each of these cell lines is known by and available to those skilled in the art of protein expression.

Similarly useful as host cells suitable for the present invention are bacterial cells. For example, the various strains of *E. coli* (e.g., HB101, (ATCC No. 33694) DH5α, DH10, and MC1061 (ATCC No. 53338)) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for expression of the polypeptides of the present invention. Preferred yeast cells include, for example, *Saccharomyces cerevisiae* and *Pichia pastoris*.

Additionally, where desired, insect cell systems may be utilized in the methods of the present invention. Such systems are described for example in Kitts et al., *Biotechniques*, 14: 810–817, 1993; Luckow, *Curr. Opin. Biotechnol.*, 4: 564–572, 1993; and Luckow et al., *J. Virol.*, 67: 4566–4579, 1993. Preferred insect cells are Sf-9 and Hi5 (Invitrogen, Carlsbad, Calif.).

One may also use transgenic animals to express glycosylated h2520-59 polypeptides. For example, one may use a transgenic milk-producing animal (a cow or goat, for example) and obtain the present glycosylated polypeptide in the animal milk. One may also use plants to produce h2520-59 polypeptides.

Polypeptide Production

Host cells comprising a h2520-59 polypeptide expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include, Roswell Park Memorial Institute medium 1640 (RPMI 1640), Minimal Essential Medium (MEM), and/or Dulbecco's Modified Eagle Medium (DMEM), all of which may be supplemented with serum and/or growth factors as indicated for the particular cell line being cultured. A suitable medium for insect cultures is Grace's medium supplemented with yeastolate, lactalbumin hydrolysate, and/or fetal calf serum, as necessary.

Typically, an antibiotic or other compound useful for selective growth of transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of a h2520-59 polypeptide produced by a host cell can be evaluated using standard methods known in the art. Such methods include, without limitation, Western blot analysis, SDS-polyacrylamide gel electrophoresis, non-denaturing gel electrophoresis, chromatographic separation such as High Performance Liquid Chromatography (HPLC), immunodetection such as immunoprecipitation, and/or activity assays such as DNA binding gel shift assays.

If a h2520-59 polypeptide has been designed to be secreted from the host cells, the majority of polypeptide may be found in the cell culture medium. If however, the h2520-59 polypeptide is not secreted from the host cells, it will be present in the cytoplasm and/or the nucleus (for eukaryotic host cells) or in the cytosol (for bacterial host cells).

For a h2520-59 polypeptide situated in the host cell cytoplasm and/or the nucleus (for eukaryotic host cells) or in the cytosol (for bacterial host cells), intracellular material (including inclusion bodies) can be extracted from the host cell using any standard technique known to the skilled artisan. For example, the host cells can be lysed to release the contents of the periplasm/cytoplasm by osmotic shock French press, homogenization, enzymatic disruption, exposure to detergents or chaotropes, and/or sonication followed by centrifugation.

If a h2520-59 polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The h2520-59 polypeptide in its now soluble form can then be analyzed using gel electrophoresis, immunoprecipitation or the like. If it is desired to isolate the h2520-59 polypeptide, isolation may be accomplished using standard methods such as those described herein and in Marston et al., Meth. Enzymol., 182:264–275, 1990.

In some cases, a h2520-59 polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a . The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cuprous chloride, dithiothreitol (DTT)/ dithiane DTT, and 2-2mercaptoethanol(bME)/ dithio-b(ME). A cosolvent may be used to increase the efficiency of the refolding, and the more common reagents used for this purpose include glycerol, polyethylene glycol of various molecular weights, arginine and the like.

If inclusion bodies are not formed to a significant degree upon expression of a h2520-59 polypeptide, then the polypeptide will be found primarily in the supernatant after centrifugation of the cell homogenate. The polypeptide may be further isolated from the supernatant using methods such as those described herein or otherwise known in the art.

The purification of a h2520-59 polypeptide from solution can be accomplished using a variety of techniques. If the polypeptide has been synthesized such that it contains a tag such as Hexahistidine (h2520-59 polypeptide/hexaHis) or other small peptide such as FLAG (Eastman Kodak Co., New Haven, Conn.) or myc (Invitrogen, Carlsbad, Calif.) at either its carboxyl or amino terminus, it may be purified in a one-step process by passing the solution through an affinity column where the column matrix has a high affinity for the tag.

For example, polyhistidine binds with great affinity and specificity to nickel; thus an affinity column of nickel (such as the Qiagen® nickel columns) can be used for purification of h2520-59 polypeptide/polyHis. See for example, Ausubel et al., eds., Current Protocols in Molecular Biology, Section 10.11.8, John Wiley & Sons, New York (1993).

Additionally, the h2520-59 polypeptide may be purified through use of a monoclonal antibody which is capable of specifically recognizing and binding to the h2520-59 polypeptide.

Suitable procedures for purification thus include, without limitation, affinity chromatography, immunoaffinity chromatography, ion exchange chromatography, molecular sieve chromatography, High Performance Liquid Chromatography (HPLC), elctrophoresis (including native gel elctrophoresis) followed by gel elution, and preparative isoelectric focusing ("Isoprime" machine/technique, Hoefer Scientific, San Francisco, Calif.). In some cases, two or more of these purification techniques may be combined to achieve increased purity.

The h2520-59 polypeptides may also be prepared by chemical synthesis methods (such as solid-phase peptide synthesis) using techniques known in the art, such as those set forth by Merrifield et al., J. Am. Chem. Soc., 85:2149, 1963, Houghten et al., Proc. Natl. Acad. Sci. USA, 82:5132, 1985, and Stewart and Young, Solid Phase Peptide Synthesis, Pierce Chemical Co., Rockford, Ill., 1984. Such polypeptides may be synthesized with or without a methionine on the amino terminus. Chemically synthesized h2520-59 polypeptides may be oxidized using methods set forth in these references to form disulfide bridges. Chemically synthesized h2520-59 polypeptides are expected to have comparable biological activity to the corresponding h2520-59 polypeptides produced recombinantly or purified from natural sources, and thus may be used interchangeably with a recombinant or natural h2520-59 polypeptide.

Another means of obtaining a h2520-59 polypeptide is via purification from biological samples such as source tissues and/or fluids in which the h2520-59 polypeptide is naturally found. Such purification can be conducted using methods for protein purification as described herein or as otherwise known in the art. The presence of the h2520-59 polypeptide during purification may be monitored, for example, using an antibody prepared against recombinantly produced h2520-59 polypeptide or peptide fragments thereof.

A number of additional methods for producing nucleic acids and polypeptides are known in the art, and the methods can be used to produce polypeptides having specificity for h2520-59. See, for example, Roberts et al., Proc. Natl. Acad. Sci. U.S.A., 94:12297–12303, 1997, which describes the production of fusion proteins between an mRNA and its encoded peptide. See also Roberts, Curr. Opin. Chem. Biol., 3:268–273, 1999. Additionally, U.S. Pat. No. 5,824,469 describes methods of obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those which exhibit a predetermined biological function. From that subpopulation, oligonucleotides capable of carrying out the desired biological function are isolated.

U.S. Pat. Nos. 5,763,192; 5,814,476; 5,723,323; and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter randomly locates a break at the front 5' end of a gene, initiating transcription of the gene. This results in expression of the desired peptide or polypeptide.

It will be appreciated that these methods can also be used to create comprehensive h2520-59-like protein expression libraries, which can subsequently be used for high throughput phenotypic screening in a variety of assays, such as biochemical assays, cellular assays, and whole organism assays (e.g. plant, mouse, etc.).

Chemical Derivatives

Chemically modified derivatives of the h2520-59 polypeptides may be prepared by one skilled in the art, given the disclosures set forth below herein. h2520-59 polypeptide derivatives are modified in a manner that is different, either in the type or location of the molecules naturally attached to the polypeptide. Derivatives may include molecules formed by the deletion of one or more naturally attached chemical groups. The polypeptide comprising the amino acid sequence of SEQ ID NO: 2, or a h2520-59 polypeptide variant, may be modified by the covalent attachment of one or more polymers. For example, the polymer selected is typically water soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa to about 35 kDa. Suitable water-soluble polymers or mixtures thereof include, but are not limited to, N-linked or O-linked carbohydrates; sugars; phosphates; polyethylene glycol (PEG) (including the forms of PEG that have been used to derivatize proteins, including mono-(C1–C10) alkoxy- or aryloxy-polyethylene glycol), monomethoxy-polyethylene glycol; dextran (such as low molecular weight dextran of, for example, about 6 kD), cellulose, or other carbohydrate-based polymers, poly-(N-vinyl pyrrolidone) polyethylene glycol, propylene glycol homopolymers, a polypropylene oxide/ethylene oxide co-polymer, polyoxyetbylated polyols (e.g., glycerol) and polyvinyl alcohol. Also encompassed by the present invention are bifunctional crosslinking molecules which may be used to prepare covalently attached multimers of the polypeptide comprising the amino acid sequence of SEQ ID NO: 2 or a h2520-59 polypeptide variant.

In general, chemical derivatization may be performed under any suitable condition used to react a protein with an activated polymer molecule. Methods for preparing chemical derivatives of polypeptides will generally comprise the steps of (a) reacting the polypeptide with the activated polymer molecule (such as a reactive ester or aldehyde derivative of the polymer molecule) under conditions whereby the polypeptide comprising the amino acid sequence of SEQ ID NO: 2, or a h2520-59 polypeptide variant becomes attached to one or more polymer molecules, and (b) obtaining the reaction product(s). The optimal reaction conditions will be determined based on known parameters and the desired result. For example, the larger the ratio of polymer molecules:protein, the greater the percentage of attached polymer molecule. In one embodiment, the h2520-59 polypeptide derivative may have a single polymer molecule moiety at the amino terminus. (See, for example, U.S. Pat. No. 5,234,784).

The pegylation of the polypeptide may be specifically carried out by any of the pegylation reactions known in the art, as described for example in the following references: Francis et al., Focus on Growth Factors, 3:4–10 (1992); EP 0154316; EP 0401384 and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, the polymer(s) selected should have a single reactive ester group. For reductive alkylation, the polymer(s) selected should have a single reactive aldehyde group. A reactive aldehyde is, for example, polyethylene glycol propionaldehyde, which is water stable, or mono C1–C10 alkoxy or aryloxy derivatives thereof (see U.S. Pat. No. 5,252,714).

In another embodiment, h2520-59 polypeptides may be chemically coupled to biotin, and the biotin/h2520-59 polypeptide molecules which are conjugated are then allowed to bind to avidin, resulting in tetravalent avidin/biotin/h2520-59 polypeptide molecules. h2520-59 polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions which may be alleviated or modulated by the administration of the present h2520-59 polypeptide derivatives include those described herein for h2520-59 polypeptides. However, the h2520-59 polypeptide derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, rabbits, or other rodents, goats, or sheep, or other farm animals, in which the gene (or genes) encoding the native h2520-59 polypeptide has (have) been disrupted ("knocked out") such that the level of expression of this gene or genes is (are) significantly decreased or completely abolished. Such animals may be prepared using techniques and methods such as those described in U.S. Pat. No. 5,557,032.

The present invention further includes non-human animals such as mice, rats, rabbits, or other rodents, goats, sheep, or other farm animals, in which either the native form of the h2520-59 gene(s) for that animal or a heterologous h2520-59 gene(s) is (are) over-expressed by the animal, thereby creating a "transgenic" animal. Such transgenic animals may be prepared using well-known methods such as those described in U.S. Pat. No. 5,489,743 and PCT Application No. WO 94/28122.

The present invention further includes non-human animals in which the promoter for one or more of the h2520-59 polypeptides of the present invention is either activated or inactivated (e.g., by using homologous recombination methods) to alter the level of expression of one or more of the native h2520-59 polypeptides.

These non-human animals may be used for drug candidate screening. In such screening, the impact of a drug candidate on the animal is measured; for example, drug candidates may decrease or increase the expression of the h2520-59 gene. In certain embodiments, the amount of h2520-59 polypeptide that is produced is measured after the exposure of the animal to the drug candidate. Additionally, in certain embodiments, one may detect the actual impact of the drug candidate on the animal. For example, the overexpression of a particular gene may result in, or be associated with, a disease or pathological condition. In such cases, one may test a drug candidate's ability to decrease expression of the gene or its ability to prevent, inhibit, or eliminate a pathological condition. In other examples, the production of a particular metabolic product such as a fragment of a polypeptide may result in, or be associated with, a disease or pathological condition. In such cases, one may test a drug candidate's ability to decrease the production of such a metabolic product or its ability to prevent, inhibit, or eliminate a pathological condition.

Microarray

It will be appreciated that DNA microarray technology can be utilized in accordance with the present invention. DNA microarrays are miniature, high density arrays of nucleic acids positioned on a solid support, such as glass. Each cell or element within the array has numerous copies of a single species of DNA which acts as a target for hybridization for its cognate mRNA. In expression profiling using DNA microarray technology, mRNA is first extracted from a cell or tissue sample and then converted enzymatically to fluorescently labeled cDNA. This material is hybridized to the micro array and unbound cDNA is removed by washing. The expression of discrete genes represented on the array is then visualized by quantitating the amount of labeled thousands of genes can be quantitated in a high-throughput, parallel manner from a single sample of biological material.

This high-throughput expression profiling has a broad range of applications with respect to the h2520-59 molecules of the invention, including, but not limited to: the identification and validation of h2520-59 disease-related genes as targets for therapeutics; molecular toxicology of h2520-59 molecules and inhibitors thereof; stratification of populations and generation of surrogate markers for clinical trials; and the enhancement of h2520-59-related small molecule drug discovery by aiding in the identification of selective compounds in high-throughput screens (HTS).

Selective Binding Agents

As used herein, the term "selective binding agent" refers to a molecule which has specificity for one or more h2520-59 polypeptides. Suitable selective binding agents include, but are not limited to, antibodies and derivatives thereof, polypeptides, and small molecules. Suitable selective binding agents may be prepared using methods known in the art. An exemplary h2520-59 polypeptide selective binding agent of the present invention is capable of binding a certain portion of the h2520-59 polypeptide, thereby inhibiting the binding of the polypeptide to the h2520-59 polypeptide receptor(s).

Selective binding agents, such as antibodies and antibody fragments that bind h2520-59 polypeptides, are within the scope of the present invention. The antibodies may be polyclonal, including monospecific polyclonal, monoclonal (MAbs), recombinant, chimeric, humanized such as CDR-grafted, human, single chain, and/or bispecific, as well as fragments, variants or derivatives thereof. Antibody fragments include those portions of the antibody which bind to an epitope on the h2520-59 polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a h2520-59 polypeptide generally are produced in animals (e.g., rabbits or mice) by means of multiple subcutaneous, intramuscular, or intraperitoneal injections of h2520-59 polypeptide and an adjuvant. It may be useful to conjugate a h2520-59 polypeptide to a carrier protein that is immunogenic in the species to be immunized, such as keyhole limpet hemocyanin, serum albumin, bovine thyroglobulin, or soybean trypsin inhibitor. Also, aggregating agents such as alum are used to enhance the immune response. After immunization, the animals are bled and the serum is assayed for anti-h2520-59 polypeptide antibody titer.

Monoclonal antibodies directed toward h2520-59 polypeptide are produced using any method which provides for the production of antibody molecules by continuous cell lines in culture. Examples of suitable methods for preparing monoclonal antibodies include the hybridoma methods of Kohler et al. (*Nature,* 256:495–497, 1975) and the human B-cell hybridoma method of Kozbor (*J. Immunol.,* 133: 3001, 1984; Brodeur et al., *Monoclonal Antibody Production Techniques and Applications,* pp. 51–63, Marcel Dekker, Inc., New York, 1987). Also provided by the invention are hybridoma cell lines which produce monoclonal antibodies reactive with h2520-59 polypeptides.

Monoclonal antibodies of the invention may be modified for use as therapeutics. One embodiment is a "chimeric" antibody in which a portion of the heavy and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567 and Morrison et al., *Proc. Natl. Acad. Sci. U.S.A.,* 81: 6851–6855 (1985).

In another embodiment, a monoclonal antibody of the invention is a "humanized" antibody. Methods for humanizing non-human antibodies are well known in the art. (see U.S. Pat. Nos. 5,585,089, and 5,693,762). Generally, a humanized antibody has one or more amino acid residues introduced into it from a source which is non-human. Humanization can be performed, for example, using methods described in the art (Jones et al., *Nature* 321: 522–525, 1986; Riechmann et al., *Nature,* 332: 323–327, 1988; Verhoeyen et al., *Science* 239:1534–1536, 1988), by substituting at least a portion of a rodent complementarity-determining region (CDR) for the corresponding region of a human antibody.

Also encompassed by the invention are human antibodies which bind h2520-59 polypeptide, fragments, variants and/or derivatives. Using transgenic animals (e.g., mice) that are capable of producing a repertoire of human antibodies in the absence of endogenous immunoglobulin production, such antibodies are produced by immunization with a h2520-59 antigen (i.e., having at least 6 contiguous amino acids), optionally conjugated to a carrier. See, for example, Jakobovits et al., *Proc. Natl. Acad. Sci. U.S.A.,* 90: 2551–2555, 1993; Jakobovits et al., *Nature* 362: 255–258, 1993; Bruggermann et al., *Year in Immunol.,* 7: 33, 1993. In one method, such transgenic animals are produced by incapacitating the endogenous loci encoding the heavy and light immunoglobulin chains therein, and inserting nucleic acids encoding human heavy and light chain proteins into the genome thereof. Partially modified animals, that is those having less than the full complement of modifications, are then cross-bred to obtain an animal having all of the desired immune system modifications. When administered an immunogen, these transgenic animals produce antibodies with human variable regions, including human (rather than, e.g., murine) amino acid sequences, including variable regions which are immunospecific for these antigens. See PCT Application Nos. PCT/US96/05928 and PCT/US93/06926. Additional methods are described in U.S. Pat. No. 5,545,807, PCT Application Nos. PCT/US91/245, PCT/GB89/01207, and in EP 546073B1 and EP 546073A1. Hunan antibodies may also be produced by the expression of recombinant DNA in host cells or by expression in hybridoma cells as described herein.

In an alternative embodiment, human antibodies can be produced from phage-display libraries (Hoogenboom et al., *J. Mol. Biol.* 227: 381, 1991; Marks et al., *J. Mol. Biol.* 222: 581, 1991). These processes mimic immune selection through the display of antibody repertoires on the surface of filamentous bacteriophage, and subsequent identification of phage by their binding to an antigen of choice. One such technique is described in PCT Application No. PCT/US98/17364, filed in the name of Adams et al., which describes the isolation of high affinity and functionally agonistic antibodies for MPL- and msk- receptors using such an approach.

Chimeric, CDR grafted, and humanized antibodies are typically produced by recombinant methods. Nucleic acids encoding the antibodies are introduced into host cells and expressed using materials and procedures described herein or known in the art. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-h2520-59 antibodies of the invention may be employed in any known assay method, such as competitive binding assays, direct and indirect sandwich assays, and immunoprecipitation assays (Sola, *Monoclonal Antibodies: A Manual of Techniques,* pp. 147–158, CRC Press, Inc., 1987) for the detection and quantitation of h2520-59 polypeptides. The antibodies will bind h2520-59 polypeptides with an affinity which is appropriate for the assay method being employed.

For diagnostic applications, in certain embodiments, anti-h2520-59 antibodies typically will be labeled with a detectable moiety. The detectable moiety can be any one which is capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, b-galactosidase, or horseradish peroxidase (Bayer et al., *Meth. Enzymol.,* 184: 138–163, 1990). Competitive binding assays rely on the ability of a labeled standard (e.g., a h2520-59 polypeptide, or an immunologically reactive portion thereof) to compete with the test sample analyte (a h2520-59 polypeptide) for binding with a limited amount of anti- h2520-59 antibody. The amount of a h2520-59 polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-h2520-59 antibodies, are also useful for in vivo imaging. An antibody labeled with a detectable moiety may be administered to an animal, preferably into the bloodstream, and the presence and location of the labeled antibody in the host is assayed. The antibody may be labeled with any moiety that is detectable in an animal, whether by nuclear magnetic resonance, radiology, or other detection means known in the art.

Selective binding agents of the invention, including anti-h2520-59 antibodies, may be used as therapeutics. These therapeutic agents are generally agonists or antagonists, in that they either enhance or reduce, respectively, at least one of the biological activities of a h2520-59 polypeptide. In one embodiment, antagonist antibodies of the invention are antibodies or binding fragments thereof which are capable of specifically binding to a h2520-59 polypeptide and which are capable of inhibiting or eliminating the functional activity of a h2520-59 polypeptide in vivo or in vitro. In preferred embodiments, the selective binding agent, e.g., an antagonist antibody, will inhibit the functional activity of a h2520-59 polypeptide by at least about 50%, and preferably by at least about 80%. In another embodiment, the selective binging agent may be an antibody that is capable of interacting with a h2520-59 binding partner (a ligand, co-factor, or receptor) thereby inhibiting or eliminating h2520-59 activity in vitro or in vivo. Selective binding agents, including agonist and antagonist anti-h2520-59 antibodies, are identified by screening assays which are well known in the art.

The invention also relates to a kit comprising h2520-59 selective binding agents (such as antibodies) and other reagents useful for detecting h2520-59 polypeptide levels in biological samples. Such reagents may include a secondary activity, a detectable label, blocking serum, positive and negative control samples, and detection reagents.

Assaying for Other Modulators of h2520-59 Polypeptide Activity

In some situations, it may be desirable to identify molecules that are modulators, i.e., agonists or antagonists, of the activity of a h2520-59 polypeptide. Natural or synthetic molecules that modulate h2520-59 polypeptide may be identified using one or more screening assays, such as those described herein. Such molecules may be administered either in an ex vivo manner, or in an in vivo manner by injection, or by oral delivery, implantation device, or the like. "Test molecule(s)" refers to the molecule(s) that is/are under evaluation for the ability to modulate (i.e., increase or decrease) an activity of a h2520-59 polypeptide. Most commonly, a test molecule will interact directly with a h2520-59 polypeptide. However, it is also contemplated that a test molecule may also modulate h2520-59 polypeptide activity indirectly, such as by affecting h2520-59 gene expression, or by binding to a h2520-59 binding partner (e.g., receptor, co-factor, or ligand). In one embodiment, a test molecule will bind to a h2520-59 polypeptide with an affinity constant of at least about $10^{-6}$ M, preferably about $10^{-8}$ M, more preferably about $10^{-9}$ M, and even more preferably about $10^{-9}$ M.

Methods for identifying compounds which interact with h2520-59 polypeptides are encompassed by the present invention. In certain embodiments, an h2520-59 polypeptide is incubated with a test molecule under conditions which permit the interaction of the test molecule with a h2520-59 polypeptide, and the extent of the interaction can be measured. The test molecule(s) can be screened in a substantially purified form or in a crude mixture.

In certain embodiments, a h2520-59 polypeptide agonist or antagonist may be a protein, peptide, carbohydrate, lipid, or small molecular weight molecule which interacts with h2520-59 polypeptide to regulate its activity. Molecules which regulate h2520-59 polypeptide expression include nucleic acids which are complementary to nucleic acid encoding a h2520-59 polypeptide, or are complementary to nucleic acids sequences which direct or control the expression of h2520-59 polypeptide, and which act as anti-sense regulators of expression.

Once a set of test molecules has been identified as interacting with a 1h2520-59 polypeptide, the molecules may be further evaluated for their ability to increase or decrease h2520-59 polypeptide activity. The measurement of the interaction of test molecules with h2520-59 polypeptides may be carried out in several formats, including cell-based binding assays, membrane binding assays, solution-phase assays and immunoassays. In general, test molecules are incubated with a h2520-59 polypeptide for a specified period of time, and h2520-59 polypeptide activity is determined by one or more assays for measuring biological activity.

The interaction of test molecules with h2520-59 polypeptides may also be assayed directly using polyclonal or monoclonal antibodies in an immunoassay. Alternatively, modified forms of h2520-59 polypeptides containing epitope tags as described herein may be used in immunoassays.

h2520-59 polypeptides displaying biological activity through an interaction with a binding partner (e.g., a receptor, a ligand or a co-factor), are assessed by a variety of in vitro assays that may be used to measure the binding of a h2520-59 polypeptide to the corresponding binding partner (such as a selective binding agent, receptor, ligand, or co-factor). These assays are used to screen test molecules for their ability to increase or decrease the rate and/or the extent of binding of a h2520-59 polypeptide to its binding partner. In one assay, a h2520-59 polypeptide is immobilized in the wells of a microtiter plate. Radiolabeled h2520-59 binding partner (for example, iodinated h2520-59 binding partner) and the test molecule(s) are added either one at a time (in either order) or simultaneously to the wells. After incubation, the wells are washed and counted using a scintillation counter, to determine the extent to which the binding partner bound to the h2520-59 polypeptide. Typically, the molecules will be tested over a range of concentrations, and a series of control wells lacking one or more elements of the test assays is used for accuracy in the evaluation of the results. An alternative to this method involves reversing the "positions" of the proteins, ie., immobilizing a h2520-59 polypeptide binding partner to the microtiter plate wells, incubating with the test molecule and radiolabeled h2520-59 polypeptide, and determining the extent of h2520-59 polypeptide binding. See, for example, chapter 18, *Current Protocols in Molecular Biology*, Ausubel et al., eds., John Wiley & Sons, New York, N.Y. (1995).

As an alternative to radiolabelling, a h2520-59 polypeptide or its binding partner may be conjugated to biotin and the presence of biotinylated protein is detected using streptavidin linked to an enzyme, such as horseradish peroxidase (HRP) or alkaline phosphatase (AP), that is detected colorimetrically, or by fluorescent tagging of streptavidin. An antibody directed to a h2520-59 polypeptide or to a h2520-59 binding partner and conjugated to biotin may also be used and is detected after incubation with enzyme-linked streptavidin linked to AP or HRP.

A h2520-59 polypeptide or a h2520-59 like binding partner can also be immobilized by attachment to agarose beads, acrylic beads or other types of such inert solid phase substrates. The substrate-protein complex is placed in a solution containing the complementary protein and the test compound. After incubation, the beads are precipitated by centrifugation, and the amount of binding between a h2520-59 polypeptide and its binding partner is assessed using the methods described herein. Alternatively, the substrate-protein complex is immobilized in a column, and the test molecule and complementary protein are passed through the column. The formation of a complex between a h2520-59 polypeptide and its binding partner is then assessed using any of the techniques set forth herein, i.e., radiolabelling, antibody binding or the like.

Another in vitro assay that is useful for identifying a test molecule that increases or decreases the formation of a complex between a h2520-59 polypeptide and a h2520-59 binding partner is a surface plasmon resonance detector system such as the BIAcore assay system (Pharmacia, Piscataway, N.J.). The BIAcore system may be carried out using the manufacturer's protocol. This assay essentially involves the covalent binding of either h2520-59 polypeptide or a h2520-59 binding partner to a dextran-coated sensor chip which is located in a detector. The test compound and the other complementary protein is then injected, either simultaneously or sequentially, into the chamber containing the sensor chip. The amount of complementary protein that binds is assessed based on the change in molecular mass which is physically associated with the dextran-coated side of the sensor chip. The change in molecular mass can be measured by the detector system.

In some cases, it may be desirable to evaluate two or more test compounds together for their ability to increase or decrease the formation of a complex between a h2520-59 polypeptide and a h2520-59 binding partner. In these cases, the assays set forth herein can be readily modified by adding such additional test compound(s) either simultaneous with, or subsequent to, the first test compound. The remainder of the steps in the assay are set forth herein.

In vitro assays such as those described herein may be used advantageously to screen large numbers of compounds for effects on complex formation by h2520-59 polypeptide and h2520-59 binding partner. The assays may be automated to screen compounds generated in phage display, synthetic peptide, and chemical synthesis libraries.

Compounds which increase or decrease the formation of a complex between a h2520-59 polypeptide and a h2520-59 binding partner may also be screened in cell culture using cells and cell lines expressing either h2520-59 polypeptide or h2520-59 binding partner. Cells and cell lines may be obtained from any mammal, but preferably will be from human or other primate, canine, or rodent sources. The binding of a h2520-59 polypeptide to cells expressing h2520-59 binding partner at the surface is evaluated in the presence or absence of test molecules, and the extent of binding may be determined by, for example, flow cytometry using a biotinylated antibody to a h2520-59 binding partner. Cell culture assays can be used advantageously to further evaluate compounds that score positive in protein binding assays described herein.

Cell cultures can also be used to screen the impact of a drug candidate. For example, drug candidates may decrease or increase the expression of the h2520-59 gene. In certain embodiments, the amount of h2520-59 polypeptide that is produced may be measured after exposure of the cell culture to the drug candidate. In certain embodiments, one may detect the actual impact of the drug candidate on the cell culture. For example, the overexpression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide may result in, or be associated with, a disease or pathological condition. In such cases, one may test a drug candidate's ability to decrease the production of such a metabolic product in a cell culture.

A yeast two hybrid system (Chien et al., *Proc. Natl. Acad. Sci. USA*, 88:9578–9583, 1991) can be used to identify novel polypeptides that bind to, or interact with, h2520-59 polypeptides. As an example, hybrid constructs comprising DNA encoding a cytoplasmic domain of a h2520-59 polypeptide fused to a yeast GAL4-DNA binding domain may be used as a two-hybrid bait plasmid. Positive clones emerging from the screening may be characterized further to identify interacting proteins.

Internalizing Proteins

The TAT protein sequence (from HIV) can be used to internalize proteins into a cell by targeting the lipid bi-layer component of the cell membrane. See, e.g., Falwell et al., *Proc. Natl. Acad. Sci. U.S.A.* 91: 664–668, 1994. For example, an 11 amino acid sequence (YGRKKRRQRRR; SEQ ID NO: 5) of the HIV TAT protein (termed the "protein transduction domain", or TAT PDT) has been shown to mediate delivery of large bioactive proteins such as β-galactosidase and p27Kip across the cytoplasmic membrane and the nuclear membrane of a cell. See Schwarze et al., *Science*, 285: 1569–1572, 1999; and Nagahara et al., *Nature Medicine*, 4: 1449–1452, 1998. Schwarze et al., supra, demonstrated that cultured cells acquired β-galactosidase activity when exposed to a fusion of the TAT PDT and β-galactosidase. Injection of mice with the TAT-β-gal fusion proteins resulted in β-gal expression in a number of tissues, including liver, kidney, lung, heart, and brain tissue.

It will thus be appreciated that the TAT protein sequence may be used to internalize a desired protein or polypeptide into a cell. In the context of the present invention, the TAT protein sequence can be fused to another molecule such as a huE3α antagonist (i.e., anti-h2520-59 selective binding agent or small molecule) and administered intracellularly to inhibit the activity of the h2520-59 molecule. Where desired, the h2520-59 protein itself, or a peptide fragment or modified form of h2520-59, may be fused to such a protein transducer for administrating to cells using the procedures described above.

Cell Source Identification using h2520-59 Polypeptides

In accordance with certain embodiments of the invention, it may be useful to be able to determine the source of a certain cell type associated with a h2520-59 polypeptide. For example, it may be useful to determine the origin of a disease or pathological condition as an aid in selecting an appropriate therapy. h2520-59 polypeptide is specifically associated with transformed cells. In certain embodiments, nucleic acids encoding a h2520-59 polypeptide can be used as a probe to identify transformed cells by screening the nucleic acids of the cells with such a probe. In other embodiments, one may use anti-h2520-59 polypeptide antibodies to test for the presence of a h2520-59 polypeptide in cells, to determine if such cells are tumor-derived.

Diseases and Therapeutic uses

In one aspect, the present invention provides reagents and methods useful for treating diseases and conditions characterized by aberrant levels of h2520-59 activity in a cell. A non-exclusive list of acute and chronic diseases which are treated, diagnosed, ameliorated, or prevented with the polypeptides, nucleic acids, antibodies, and/or fragments thereof of the invention include hyperproliferative pathological conditions such as immune disorders, angiogenesis, vasculogenesis, wound healing, diabetes mellitus including diabetes type I and type II, psoriasis, liver diseases such as hepatitis and cirrhosis, osteoporosis, inflammatory conditions such as osteoarthritis and rheumatoid arthritis, pregnancy and cancer.

More specifically, the types of cancers and tumor cells that are treated, diagnosed, ameliorated or prevented with h2520-59 polypeptides, nucleic acids, antibodies, and/or fragments thereof include, but are not limited to, ACTH-producing tumors, acute lymphocytic leukemias, acute non-lymphocytic leukemias, cancers of the adrenal cortex, bladder cancer, brain cancer, breast cancer, cervical cancer, chronic lymphocytic leukemias, chronic myelocytic leukemias, colorectal cancer, cutaneous T-cell lymphomas, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and non-small cell), malignant peritoneal effusion, malignant pleural effusion, melanoma, mesothelioma, multiple myeloma, neuroblastoma, glioma, non-Hodgkin's lymphoma, osteosarcoma, ovarian cancer, ovarian (germ cell) cancer, pancreatic cancer, penile cancer, prostate cancer, retinoblastoma, skin cancer, soft tissue sarcoma, squamous cell carcinoma, stomach cancer, testicular cancer, thyroid cancer, trophoblastic neoplasms, uterine cancer, vaginal cancer, cancer of the vulva, Wilms' tumor, adenocarcinoma of the breast, prostate, and colon, all forms of bronchogenic carcinoma of the lung, myeloid, melanoma, hepatoma, neuroblastoma, papilloma, apudoma, choristoma, branchioma, malignant carcinoid syndrome, carcinoid heart disease, carcinoma (e.g., Walker, basal cell, basosquamous, Brown-Pearce, ductal, Ehrlich tumor, Krebs 2, Merkel's cell, mucinous, non-small cell lung, oat cell, papillary, scirrhous, bronchiolar, bronchogenic, squamous cell, and transitional cell). Additional types of cancers that may be treated include histiocytic disorders, leukemia, histiocytosis malignant, Hodgkin's disease, immunoproliferative small, non-Hodgkin's lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, chordoma, craniopharyngioma, dysgerminoma, hamartoma, mesenchyrnoma, mesonephroma, myosarcoma, ameloblastoma, cementoma, odontoma, teratoma, thymoma, and trophoblastic tumor. Further, the following types of cancers may also be treated: adenoma, cholangioma, cholesteatoma, cyclindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, and paraganglioma nonchromaffin. The types of cancers that may be treated also include, but are not limited to, the following: angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, careinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma, neoplasms, nerofibromatosis, and cervical dysplasia.

The invention further provides compositions and methods useful for treatment of other conditions in which cells have become immortalized or hyperproliferative due to abnormally high expression of h2520-59.

Other diseases or disorders caused or mediated by undesirable levels of h2520-59 polypeptide are contemplated by the therapeutic and diagnostic methods of the invention. By way of illustration, such undesirable levels include excessively elevated levels and sub-normal levels.

h2520-59 Compositions and Administration

Therapeutic compositions within the scope of the present invention include h2520-59 pharmaceutical compositions that may comprise a therapeutically effective amount of a h2520-59 polypeptide or a h2520-59 nucleic acid molecule in admixture with a pharmaceutically or physiologically acceptable formulation agent selected for suitability with the mode of administration to a human or non-human animal such as a mammal. Pharmaceutical compositions may comprise a therapeutically effective amount of one or more h2520-59 selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol, or sorbitol); delivery vehicles; diluents; excipients and/or pharmaceutical adjuvants. (*Remington's Pharmaceutical Sciences*, 18th Edition, A. R. Gennaro, ed., Mack Publishing Company, 1990).

The optimal pharmaceutical composition will be determined by one skilled in the art depending upon, for example, the intended route of administration, delivery format, and desired dosage. See, for example, *Remington's Pharmaceutical Sciences*, supra. Such compositions may influence the physical state, stability, rate of in vivo release, and rate of in vivo clearance of the h2520-59 molecule.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0–8.5, or acetate buffer of about pH 4.0–5.5, which may farther include sorbitol or a suitable substitute therefor. In one embodiment of the present invention, h2520-59 polypeptide compositions may be prepared for storage by mixing the selected composition having the desired degree of purity with optional formulation agents (*Remington's Pharmaceutical Sciences*, supra) in the form of a lyophilized cake or an aqueous solution. Further, the h2520-59 polypeptide product may be formulated as a lyophilizate using appropriate excipients such as sucrose.

The h2520-59 pharmaceutical compositions can be selected for parenteral delivery. Alternatively, the compositions may be selected for inhalation or for delivery through the digestive tract, such as orally, or through other delivery routes known in the art. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired h2520-59 molecule in a pharmaceutically acceptable vehicle. A particularly suitable vehicle for parenteral injection is sterile distilled water in which a h2520-59 molecule is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, a h2520-59-like molecule may be formulated as a dry powder for inhalation. h2520-59 polypeptide or h2520-59 nucleic acid molecule inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, h2520-59 molecules which are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the h2520-59 molecule. Diluents, flavorings, low melting point waxes, vegetable oils, lubricants, suspending agents, tablet disintegrating agents, and binders may also be employed.

Another pharmaceutical composition may involve an effective quantity of h2520-59 molecules in a mixture with non-toxic excipients which are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional h2520-59 pharmaceutical compositions will be evident to those skilled in the art, including formulations involving h2520-59 polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 which describes controlled release of porous polymeric microparticles for the delivery of pharmaceutical compositions. Additional examples of sustained-release preparations include semipermeable polymer matrices in the form of shaped articles, e.g., films or microcapsules. Sustained release matrices may include polyesters, hydrogels, polylactides (U.S. Pat. No. 3,773,919; EP 58,481), copolymers of L-glutamic acid and gamma ethyl-L-glutamate (Sidman et al., *Biopolymers,* 22:547–556, 1983), poly (2-hydroxyethyl-methacrylate) (Langer et al., *J. Biomed. Mater. Res.,* 15:167–277, 1981; Langer et al., *Chem. Tech.,* 12:98–105, 1982), ethylene vinyl acetate (Langer et al., supra) or poly-D(−)-3-hydroxybutyric acid (EP 133,988). Sustained-release compositions also include liposomes, which can be prepared by any of several methods known in the art. See, e.g., Eppstein et al., *Proc. Natl. Acad. Sci. USA,* 82:3688–3692, 1985; EP 36,676; EP 88,046; EP 143,949.

The h2520-59 pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a h2520-59 pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the h2520-59 molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg.

The frequency of dosing will depend upon the pharmacokinetic parameters of the h2520-59 molecule in the formulation used. Typically, a clinician will administer the composition until a dosage is reached that achieves the desired effect. The composition may therefore be administered as a single dose, or as two or more doses (which may or may not contain the same amount of the desired molecule) over time, or as a continuous infusion via implantation device or catheter. Further refinement of the appropriate dosage is routinely made by those of ordinary skill in the art and is within the ambit of tasks routinely performed by them. Appropriate dosages may be ascertained through use of appropriate dose-response data, which is routinely obtained.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes, by sustained release systems or by implantation devices. Where desired, the compositions may be administered by bolus injection or continuously by infusion, or by implantation device.

Alternatively or additionally, the composition may be administered locally via implantation of a membrane, sponge, or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use h2520-59 pharmaceutical compositions in an ex vivo manner. In such instances, cells, tissues, or organs that have been removed from the patient are exposed to h2520-59 pharmaceutical compositions after which the cells, tissues and/or organs are subsequently implanted back into the patient.

In other cases, a h2520-59 polypeptide can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally silent h2520-59 gene, or an underexpressed gene, and thereby produce a cell which expresses therapeutically efficacious amounts of h2520-59 polypeptides.

Homologous recombination is a technique originally developed for targeting genes to induce or correct mutations in transcriptionally active genes (Kucherlapati et al., *Prog. Nucl. Acid Res. & Mol. Biol.*, 36:301, 1989). The basic technique was developed as a method for introducing specific mutations into specific regions of the mammalian genome (Thomas et al., *Cell*, 44:419–428, 1986; Thomas and Capecchi, *Cell*, 51:503–512, 1987; Doetschman et al., *Proc. Natl. Acad. Sci. USA*, 85:8583–8587, 1988) or to correct specific mutations within defective genes (Doetschman et al, *Nature*, 330:576–578,1987). Exemplary homologous recombination techniques are described in U.S. Pat. No. 5,272,071 (EP 9193051, EP Publication No. 505500; PCT/US90/07642, International Publication No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA which may interact with or control the expression of a h2520-59 polypeptide, e.g., flanking sequences. For example, a promoter/enhancer element, a suppressor, or an exogenous transcription modulatory element is inserted in the genome of the intended host cell in proximity and orientation sufficient to influence the transcription of DNA encoding the desired h2520-59 polypeptide. The control element controls a portion of the DNA present in the host cell genome. Thus, the expression of the desired h2520-59 polypeptide may be achieved not by transfection of DNA that encodes the h2520-59 gene itself, but rather by the use of targeting DNA (containing regions of homology with the endogenous gene of interest) coupled with DNA regulatory segments that provide the endogenous gene sequence with recognizable signals for transcription of a h2520-59 polypeptide.

In an exemplary method, the expression of a desired targeted gene in a cell (i.e., a desired endogenous cellular gene) is altered via homologous recombination into the cellular genome at a preselected site, by the introduction of DNA which includes at least a regulatory sequence, an exon and a splice donor site. These components are introduced into the chromosomal (genomic) DNA in such a manner that this, in effect, results in the production of a new transcription unit (in which the regulatory sequence, the exon and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, h2520-59 polypeptide production from a cell's endogenous h2520-59 gene involves first using homologous recombination to place a recombination sequence from a site-specific recombination system (e.g., Cre/loxP, FLP/FRT) (Sauer et al., *Curr. Opin. Biotech.*, 5:521–527, 1994; Sauer et al., *Meth. Enzymol.*, 225:890–900, 1993) upstream (that is, 5' to) of the cell's endogenous genomic h2520-59 polypeptide coding region. A plasmid containing a recombination site homologous to the site that was placed just upstream of the genomic h2520-59 polypeptide coding region is introduced into the modified cell line along with the appropriate recombinase enzyme. This recombinase causes the plasmid to integrate, via the plasmid's recombination site, into the recombination site located just upstream of the genomic h2520-59 polypeptide coding region in the cell line (Baubonis and Sauer, *Nucl. Acids Res.*, 21:2025–2029, 1993; O'Gorman et al., *Science*, 251:1351–1355, 1991). Any flanking sequences known to increase transcription (e.g., enhancer/promoter, intron, translational enhancer), if properly positioned in this plasmid, would integrate in such a manner as to create a new or modified transcriptional unit resulting in de novo or increased h2520-59 polypeptide production from the cell's endogenous h2520-59 gene.

A further method to use the cell line in which the site-specific recombination sequence had been placed just upstream of the cell's endogenous genomic h2520-59 polypeptide coding region is to use homologous recombination to introduce a second recombination site elsewhere in the cell line's genome. The appropriate recombinase enzyme is then introduced into the two-recombination-site cell line, causing a recombination event (deletion, inversion, translocation) (Sauer et al., *Curr. Opin. Biotech.*, supra; Sauer, *Meth. Enzymol.*, supra) that would create a new or modified transcriptional unit resulting in de novo or increased h2520-59 polypeptide production from the cell's endogenous h2520-59 gene.

An additional approach for increasing, or causing, the expression of h2520-59 polypeptide from a cell's endogenous h2520-59 gene involves increasing, or causing, the expression of a gene or genes (e.g. transcription factors) and/or decreasing the expression of a gene or genes (e.g., transcriptional repressors) in a manner which results in de novo or increased h2520-59 polypeptide production from the cell's endogenous h2520-59 gene. This method includes the introduction of a non-naturally occurring polypeptide (e.g., a polypeptide comprising a site specific DNA binding domain fused to a transcriptional factor domain) into the cell such that de novo or increased h2520-59 polypeptide production from the cell's endogenous h2520-59 gene results.

The present invention further relates to DNA constructs useful in the method of altering expression of a target gene. In certain embodiments, the exemplary DNA constructs comprise: (a) one or more targeting sequences; (b) a regulatory sequence; (c) an exon; and (d) an unpaired splice-donor site. The targeting sequence in the DNA construct directs the integration of elements (a)–(d) into a target gene in a cell such that the elements (b)–(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)–(f) such that the elements of (b)–(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of h2520-59 polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence(s) upon insertion into the cell in that it will hybridize to its homologous region within the genome. It is conventionally believed that if this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a h2520-59 polypeptide, which nucleotides may be used as targeting sequences.

h2520-59 polypeptide cell therapy, e.g., the implantation of cells producing h2520-59 polypeptides, is also contemplated. This embodiment involves implanting cells capable of synthesizing and secreting a biologically active form of h2520-59 polypeptide. Such h2520-59 polypeptide-producing cells can be cells that are natural producers of h2520-59 polypeptides or may be recombinant cells whose ability to produce h2520-59 polypeptides has been augmented by transformation with a gene encoding the desired h2520-59 polypeptide or with a gene augmenting the expression of h2520-59 polypeptide. Such a modification may be accomplished by means of a vector suitable for delivering the gene as well as promoting its expression and secretion. In order to minimize a potential immunological reaction in patients being administered a h2520-59 polypeptide, as may occur with the administration of a polypeptide of a foreign species, it is preferred that the natural cells producing h2520-59 polypeptide be of human origin and produce human h2520-59 polypeptide. Likewise, it is preferred that the recombinant cells producing h2520-59 polypeptide be transformed with an expression vector containing a gene encoding a human h2520-59 polypeptide.

Implanted cells may be encapsulated to avoid the infiltration of surrounding tissue. Human or non-human animal cells may be implanted in patients in biocompatible, semipermeable polymeric enclosures or membranes that allow the release of h2520-59 polypeptide, but prevent the destruction of the cells by the patient's immune system or by other detrimental factors from the surrounding tissue. Alternatively, the patient's own cells, transformed to produce h2520-59 polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (WO95/05452; PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for delivery of the molecules from living cells to specific sites within a recipient. In addition, see U.S. Pat. Nos. 4,892,538, 5,011,472, and 5,106,627. A system for encapsulating living cells is described in PCT Application No. PCT/US91/00157 of Aebischer et al. See also, PCT Application No. PCT/US91/00155 of Aebischer et al.; Winn et al., *Exper. Neurol.*, 113: 322–329, 1991; Aebischer et al., *Exper. Neurol.*, 111:269–275, 1991; and Tresco et al., *ASAIO*, 38:17–23, 1992.

In vivo and in vitro gene therapy delivery of h2520-59 polypeptides is also envisioned. One example of a gene therapy technique is to use the h2520-59 gene (either genomic DNA, cDNA, and/or synthetic DNA) encoding a h2520-59 polypeptide which may be operably linked to a constitutive or inducible promoter to form a "gene therapy DNA construct." The promoter may be homologous or heterologous to the endogenous h2520-59 gene, provided that it is active in the cell or tissue type into which the construct will be inserted. Other components of the gene therapy DNA construct may optionally include DNA molecules designed for site-specific integration (e.g., endogenous sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell-specific binding agents (as, for example, for cell targeting), cell-specific internalization factors, and transcription factors to enhance expression by a vector as well as factors to enable vector manufacture.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain unintegrated.

In yet other embodiments, regulatory elements can be included for the controlled expression of the h2520-59 gene in the target cell. Such elements are turned on in response to an appropriate effector. In this way, a therapeutic polypeptide can be expressed when desired. One conventional control means involves the use of small molecule dimerizers or rapalogs [as described in WO 96/41865 (PCT/US96/099486); WO 97/31898 (PCT/US97/03137) and WO 97/31899 (PCT/US95/03157)] used to dimerize chimeric proteins which contain a small-molecule binding domain and a domain capable of initiating biological process, such as a DNA-binding protein or transcriptional activation protein. The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain which results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See, Aridor and Balch, Science 287:816–817, 2000; Rivera et al., Science 287:826–830, 2000.

Other suitable control means or gene switches include, but are not limited to, the following systems. Mifepristone (RU486) is used as a progesterone antagonist. The binding of a modified progesterone receptor ligand-binding domain to the progesterone antagonist activates transcription by forming a dimer of two transcription factors which then pass into the nucleus to bind DNA. The ligand-binding domain is modified to eliminate the ability of the receptor to bind to the natural ligand. The modified steroid hormone receptor system is further described in U.S. Pat. No. 5,364,791; WO 96/40911; and WO 97/10337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain/DNA-binding domain/ligand-binding domain to initiate transcription. The ecdysone system is further described in U.S. Pat. No. 5,514,578; WO 97/38117; WO 96/37609; and WO 93/03162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758, 5,650,298 and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding a h2520-59 polypeptide into cells via local injection of a h2520-59 nucleic acid molecule or by other appropriate viral or non-viral delivery vectors. See, Hefti, Neurobiology, 25:1418–1435, 1994. For example, a nucleic acid molecule encoding a h2520-59 polypeptide may be contained in an adeno-associated virus (AAV) vector for delivery to the targeted cells (e.g., Johnson, International Publication No. WO 95/34670; International Application No. PCT/US95/07178). The recombinant AAV genome typically contains AAV inverted terminal repeats flanking a DNA sequence encoding a h2520-59 polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, pararnyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 involving adenoviral vectors; U.S. Pat. No. 5,672,510 involving retroviral vectors; and U.S. Pat. No. 5,635,399 involving retroviral vectors expressing cytokines.

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include the use of inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 involving electroporation techniques; WO96/40958 involving nuclear ligands; U.S. Pat. No. 5,679,559 describing a lipoprotein-containing system for gene delivery; U.S. Pat. No. 5,676,954 involving liposome carriers; U.S. Pat. No. 5,593,875 concerning methods for calcium phosphate transfection; and U.S. Pat. No. 4,945,050 wherein biologically active particles are propelled at cells at a speed whereby the particles penetrate the surface of the cells and become incorporated into the interior of the cells.

It is also contemplated that h2520-59 gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous h2520-59 polypeptide expression in a cell via gene therapy is to insert one or more enhancer element(s) into the h2520-59 polypeptide promoter, where the enhancer element(s) can serve to increase transcriptional activity of the h2520-59 gene. The enhancer element(s) used will be selected based on the tissue in which one desires to activate the gene(s); enhancer elements known to confer promoter activation in that tissue will be selected. For example, if a gene encoding a h2520-59 polypeptide is to be "turned on" in T-cells, the lck promoter enhancer element may be used. Here, the functional portion of the transcriptional element to be added may be inserted into a fragment of DNA containing the h2520-59 polypeptide promoter (and optionally, inserted into a vector and/or 5' and/or 3' flag sequence(s), etc.) using standard cloning techniques. This construct, known as a "homologous recombination construct," can then be introduced into the desired cells either ex vivo or in vivo.

Gene therapy also can be used to decrease h2520-59 polypeptide expression by modifying the nucleotide sequence of the endogenous promoter(s). Such modification is typically accomplished via homologous recombination methods. For example, a DNA molecule containing all or a portion of the promoter of the h2520-59 gene(s) selected for inactivation can be engineered to remove and/or replace pieces of the promoter that regulate transcription. For example the TATA box and/or the binding site of a transcriptional activator of the promoter may be deleted using standard molecular biology techniques; such deletion can inhibit promoter activity thereby repressing the transcription of the corresponding h2520-59 gene. The deletion of the TATA box or the transcription activator binding site in the promoter may be accomplished by generating a DNA construct comprising all or the relevant portion of the h2520-59 polypeptide promoter(s) (from the same or a related species as the h2520-59 gene(s) to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. The construct will typically contain at least about 500 bases of DNA that correspond to the native (endogenous) 5' and 3' DNA sequences adjacent to the promoter segment that has been modified. The construct may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Additional Uses of h2520-59 Nucleic Acids and Polypeptides

Nucleic acid molecules of the present invention (including those that do not themselves encode biologically active polypeptides) may be used to map the locations of the h2520-59 gene and related genes on chromosomes. Mapping may be done by techniques known in the art, such as PCR amplification and in situ hybridization.

The full coding region of the h2520-59 gene is contained in the human chromosome 20 sequence as listed in GENBANK Accession No. AL034548. The human 2520-59 gene is specifically localized to chromosome 20p12.2-13 134952-152220 which includes intronlexon boundaries.

h2520-59 RNA levels are elevated in a wide range of human primary tumors. Expression has been observed in brain, colon, lung, skin, bone marrow, prostate, kidney, testis, uterus, and cervix cancers. (See Examples 2 and 6). Based on the presence of a putative kinase catalytic domain in the amino acid sequence, h2520-59 polypeptide may play a role in maintaining transformed phenotypes. (See Example 1).

h2520-59 nucleic acid molecules (and related molecules that do not themselves encode biologically active polypeptides), may be useful as hybridization probes in diagnostic assays to test, either qualitatively or quantitatively, for the presence of a h2520-59 DNA or corresponding RNA in mammalian tissue orbodily fluid samples. h2520-59 may serve as a diagnosis/prognosis marker or assay for a wide variety of human cancers. Monitoring changes in the expression of h2520-59 during cancer treatment may be used as a surrogate marker to monitor tumor growth and treatment success.

The h2520-59 polypeptides may be used (simultaneously or sequentially) in combination with one or more cytokines, growth factors, antibiotics, anti-inflammatories, and/or chemotherapeutic agents as is appropriate for the indication being treated. h2520-59 may be useful as an inhibitor. In addition, peptide inhibitors designed from h2520-59 polypeptide may be used as therapeutics or identifying substances which modulate h2520-59 polypeptide activity.

Other methods may also be employed where it is desirable to inhibit the activity of one or more h2520-59 polypeptides. Such inhibition may be effected by nucleic acid molecules which are complementary to and hybridize to expression control sequences (triple helix formation) or to h2520-59 mRNA. For example, antisense DNA or RNA molecules, which have a sequence that is complementary to at least a portion of the selected b2520-59 gene(s), can be introduced into the cell. Antisense probes may be designed by available techniques using the sequence of h2520-59 polypeptide disclosed herein. Typically, each such antisense molecule will be complementary to the start site (5' end) of each selected h2520-59 gene. When the antisense molecule then hybridizes to the corresponding h2520-59 mRNA, translation of this mRNA is prevented or reduced. Antisense inhibitors provide information relating to the decrease or absence of a h2520-59 polypeptide in a cell or organism.

Alternatively, gene therapy may be employed to create a dominant-negative inhibitor of one or more h2520-59 polypeptides. In this situation, the DNA encoding a mutant polypeptide of each selected h2520-59 polypeptide can be prepared and introduced into the cells of a patient using either viral or non-viral methods as described herein. Each such mutant is typically designed to compete with endogenous polypeptide in its biological role. Particularly, h2520-59 contains a kinase domain that may be useful in designing dominant negative gene therapy for treatment in a wide variety of tumors.

In addition, a h2520-59 polypeptide, may be used as an immunogen, that is, the polypeptide contains at least one epitope to which antibodies may be raised. Selective binding agents that bind to a h2520-59 polypeptide (as described herein) may be used for in vivo and in vitro diagnostic purposes, including, but not limited to, use in labeled form to detect the presence of h2520-59 polypeptide in a body fluid or cell sample. The antibodies may also be used to prevent, treat, or diagnose a number of diseases and disorders, including those recited herein. The antibodies may bind to a h2520-59 polypeptide so as to diminish or block at least one activity characteristic of a h2520-59 polypeptide, or may bind to a polypeptide to increase at least one activity characteristic of a h2520-59 polypeptide (including by increasing the pharmacokinetics of the h2520-59 polypeptide).

cDNA encoding h2520-59 polypeptide in *E. coli* strain TOP10 was deposited with the ATCC on Apr. 25, 2000 and has Accession No. PTA-1759.

The following examples are intended for illustration purposes only, and should not be construed as limiting the scope of the invention in any way.

EXAMPLE 1

Cloning of Human h2520-59

Materials and methods for cDNA cloning and analysis are described in Sambrook et al., supra.

A search was performed on the Celera genomic database to identify potential kinases. This search identified an EST sequence, reference no. GA 6736448-150850-151365, as set out in (SEQ ID NO: 12) as a putative serine threonine (ser/thr) kinase.

Polymerase chain reaction (PCR) primers were designed based on the identified sequence to generate a 200 base pair product. The forward primer was 5' TGG TGC TGG AGA ACC TGG AGG 3' (SEQ ID NO: 3) and the reverse primer was 5' CGA GTC CTG GAA GTA GTG 3' (SEQ ID NO: 4). These primers were then used to screen the lung Rapid-Screen™ cDNA Library Panel according to the manufacturer's instructions (Origene Technologies, Rockville, Md.). PCR was carried out with 40 nM of both the forward and reverse primers, 20 µl of $H_2O$, 5 µl of the cDNA library, and 1 Ready-To-Go PCR bead (Amersham Phammacia Biotech). The PCR reaction conditions were 94° C. for 3 minutes, followed by 30 cycles of 30 seconds at 94° C., 45 seconds at 58° C., 1 minute at 72° C., and a subsequent incubation for 7 minutes at 72° C. at the end of the 30th cycle. The PCR reactions were analyzed on a 2% agarose gel and positive reactions contained a 200 base pair band.

The corresponding subplates within the lung Rapid-Screen™ cDNA Library Panel were screened using the PCR conditions described above. The positive wells were then screened according to the Rapid-Screen cDNA Library Panel using the above-described PCR conditions. The plasmid DNA from the positive wells was prepared with the Qiagen Spin Mini-Prep Kit according to the manufacturer's instruction. The sequence of both strands of the cDNA insert were verified by standard sequencing techniques.

The cDNA sequence encoding the h2520-59 polypeptide is shown in FIG. 1 (SEQ ID NO: 1). The h2520-59 gene is 2059 nucleotides in length with a 1074 nucleotide coding region. This coding region encodes a 358 amino acid polypeptide (SEQ ID NO: 2). Alignment of the deduced amino acid sequence with known ser/thr kinases determined h2520-59 polypeptide contained a putative kinase domain about three quarters toward the C-terminus. Sequence homology of the putative kinase domain revealed 26% homology with other members of the ser/thr kinase family such as RIP1, Rat Death Domain, Cdk2, and C8FW within the kinase domain.

h2520-59 amino acid sequence was determined to be closely related to NIPK (Neuronal cell death Inducible Putative Kinase) which was described by Mayumi-Matsuda et al. (*Biochem. Biophys. Res. Comm.* 258: 260–264, 1999). NIPK is 78% identical to the h2520-59 amino acid sequence and may represent the rat ortholog. The full coding region of h2520-59 is contained within the human chromosome 20 sequence described in GENBANK accession no. AL34548 and is specifically localized to chromosome p2012.2–13 134952-152220, including intron/exon boundaries.

EXAMPLE 2

Evaluation of Tissue Expression of h2520-59

A. Matched cDNA Pair Expression Analysis

To determine if h2520-59 mRNA was elevated in tumor cells as compared to normal cells, matched cDNA pair expression analysis was performed. Selected matched cDNA pair libraries (Clontech Laboratories, Palo Alto, Calif.) were screened by PCR. The PCR reactions were performed under the conditions described in Example 1. The PCR reactions were analyzed on a 4–20% acrylamide TBE gel.

The matched cDNA pairs consisted of corresponding tumor and normal cDNA libraries isolated from the same individual. These pairs allowed for the determination of elevated gene expression in tumor tissues as compared to normal tissue from the same patient. Prostate, lung, colon, ovary and uterus tissues were screened. The h2520-59 RNA expression was elevated in lung squamous cell carcinoma from a 73-year-old male (lot no. 9090813), colon adenocarcinoma from a 61-year-old female (lot no. 9080438), colon adenocarcinoma from a 75-year-old male (lot no. 9110789), colon adenocarcinoma from a 58-year-old male (lot no. 9100415), colon adenocarcinoma from a 79-year-old female (lot no. 9100394), colon adenocarcinoma from a 35-year-old female (lot no. 9100396), colon adenocarcinoma from an individual of unknown age and gender (lot no. 9100395), and ovarian serous cystadenocarcinoma for a 61-year-old female (lot no. 9090814).

B. Northern Blot Analysis

Differential tissue expression patterns of h2520-59 mRNA determined by the matched cDNA pair analysis were verified by Northern blot analysis. The probe was generated by performing PCR as described in Example 1 on the Lung Marathon-Ready™ cDNA library (Clontech, Palo Alto, Calif.). The resulting 200-base-pair product was isolated from an agarose gel and TOPO TA cloned using the TA Cloning Kit® according to the manufacturer's instructions (Invitrogen, Carlsbad Calif.). The 200-base-pair cDNA was radiolabeled with dCTP using a random primer labeling kit (Boehringer Mannheim, Indianapolis, Ind.).

Northern blot analysis was performed with human lung tumor Multi-type NBA blots (Biochain, Hayward, Calif.; lot no. 8910072) which contained tumor samples paired with normal controls and were normalized to the total amount of mRNA loaded (NBA). The blots were prehybridized in buffer containing 5×SSPE, 50% formamide, 5× Denhardt's solution, 0.5% SDS and 100 g/ml of denatured salmon sperm DNA for 3 hours at 42° C. The blots were then hybridized in the above-described buffer containing 50 ng/ml of $^{32}P$-labeled probe for 20 hours at 42° C. The blots were washed 3 times in 2×SSC/0.05% SDS for 15 minutes at room temperature. Subsequently, the blots were washed 3 times in 0.01×SSC/0.01% SDS for 20 minutes at 50° C. Radioactive blots were exposed overnight to a phosphoimaging screen and visualized with a phosphoimager (Molecular Dynamics, Sunnyvale, Calif.).

The lung tumor multi-type blot contained mRNA from poorly- to moderately-differentiated squamous cell carcinoma, poorly-differentiated squamous cell carcinoma, bronchio-alveolar carcinoma, and normal tissue. h2520-59 mRNA was overexpressed in poorly- to moderately-differentiated squamous cell carcinoma and bronchio-alveolar carcinoma as compared to the normal lung tissue (control).

h2520-59 mRNA expression was also observed in brain, colon, lung, skin, bone marrow, prostate, kidney, testis, uterus and cervix cancer tissues using the human Rapid Scan Panel according to the manufacturer's instructions (Origene, Rockville, Md.). Ts panel was screened using the PCR primers and conditions described in Example 1.

EXAMPLE 3

Production of h2520-59 Polypeptides

A. Bacterial Expression

PCR is used to amplify template DNA sequences encoding a h2520-59 polypeptide using primers corresponding to the 5' and 3' ends of the sequence. The 5' end primer has the sequence: 5'CGGGGCGAGATGCGAGCCAC3' (SEQ ID NO: 6) and the 3' end primer has the sequence: 5'AGGGTG-GTCCTAGCCATACA3' (SEQ ID NO: 7). The amplified DNA products may be modified to contain restriction enzyme sites to allow for insertion into expression vectors. PCR products are gel purified and inserted into expression vectors using standard recombinant DNA methodology. An exemplary vector, such as pAMG21 (ATCC No.98113) containing the lux promoter and a gene encoding kanamycin resistance is digested with BamHI and NdeI for directional cloning of inserted DNA. The ligated mixture is transformed into an E. coli host strain by electroporation and transformants are selected for kanamycin resistance. Plasmid DNA from selected colonies is isolated and subjected to DNA sequencing to confirm the presence of the insert.

Transformed host cells are incubated in 2×YT medium containing 30 mg/ml kanamycin at 30° C. prior to induction. Gene expression is induced by the addition of N-(3-oxohexanoyl)d1-homoserine lactone to a final concentration of 30 ng/ml followed by incubation at either 30° C. or 37° C. for six hours. The expression of h2520-59 polypeptide is evaluated by centrifugation of the culture, resuspension and lysis of the bacterial pellets, and analysis of host cell proteins by SDS-polyacrylamide gel electrophoresis.

Inclusion bodies containing h2520-59 polypeptide are purified as follows. Bacterial cells are pelleted by centrifugation and resuspended in water. The cell suspension is lysed by sonication and pelleted by centrifugation at 195,000×g for 5 to 10 minutes. The supernatant is discarded, and the pellet is washed and transferred to a homogenizer. The pellet is homogenized in 5 ml of a Percoll solution (75% liquid Percoll, 0.15 M NaCl) until uniformly suspended and then diluted and centrifuged at 21,600×g for 30 minutes. Gradient fractions containing the inclusion bodies are recovered and pooled. The isolated inclusion bodies are analyzed by SDS-PAGE.

A single band on an SDS polyacrylamide gel corresponding to E. coli-produced h2520-59 polypeptide is excised from the gel, and the N-terminal amino acid sequence is determined essentially as described by Matsudaira et al. (J. Biol. Chem., 262:10–35, 1987).

B. Mammalian Cell Production

PCR is used to amplify template DNA sequences encoding a h2520-59 polypeptide using primers corresponding to the 5' and 3' ends of the sequence. The primer sequences corresponding to the 5' and 3' ends are described above. The amplified DNA products may be modified to contain restriction enzyme sites to allow for insertion into expression vectors. PCR products are gel purified and inserted into expression vectors using standard recombinant DNA methodology. An exemplary expression vector, pCEP4 (Invitrogen, Carlsbad, Calif.), which contains an Epstein-Barr virus origin of replication, may be used for the expression of h2520-59 in 293-EBNA-1 (Epstein-Barr virus nuclear antigen) cells. Amplified and gel-purified PCR products are ligated into the pCEP4 vector and lipofected into 293-EBNA cells. The transfected cells are selected in 100 mg/ml hygromycin and the resulting drug-resistant cultures are grown to confluence. The cells are then cultured in serum-free medium for 72 hours. The conditioned medium is removed and h2520-59 polypeptide expression is analyzed by SDS-PAGE.

h2520-59 polypeptide expression may be detected by silver staining. Alternatively, h2520-59 polypeptide is produced as a fusion protein with an epitope tag, such as an IgG constant domain or a FLAG epitope, which may be detected by Western blot analysis using antibodies to the tag peptide.

h2520-59 polypeptides may be excised from an SDS-polyacrylamide gel, or h2520-59 fusion proteins are purified by affinity chromatography to the epitope tag, and subjected to N-terminal amino acid sequence analysis as described herein.

EXAMPLE 4

Production of Anti-h2520-59 Polypeptide Antibodies

Antibodies to h2520-59 polypeptides may be obtained by the immunization of animals with purified protein or with h2520-59 peptides produced by biological or chemical synthesis. Suitable procedures for generating antibodies include those described in Hudson and Hay, *Practical Immunology*, 2nd Edition, Blackwell Scientific Publications (1980).

In one procedure for the production of antibodies, animals (typically mice or rabbits) are injected with a h2520-59 antigen (such as a h2520-59 polypeptide), and those with sufficient serum titer levels, as determined by ELISA, are selected for hybridoma production. Spleens of immunized animals are collected and prepared as single cell suspensions from which splenocytes are recovered. The splenocytes are fused to mouse myeloma cells (such as Sp2/0-Ag14 cells; ATCC No. CRL1581), allowed to incubate in DMEM with 200 U/ml penicillin, 200 mg/ml streptomycin sulfate, and 4 mM glutamine, then incubated in HAT selection medium (Hypoxanthine; Aminopterin; Thymidine). After selection, the tissue culture supernatants are taken from each well containing a hybridoma and tested for anti-h2520-59 antibody production by ELISA.

Alternative procedures for obtaining anti-h2520-59 antibodies may also be employed, such as the immunization of transgenic mice harboring human Ig loci for the production of human antibodies, and the screening of synthetic antibody libraries, such as those generated by mutagenesis of an antibody variable domain.

EXAMPLE 5

Biological Activity of h2520-59 Polypeptides

Analysis of the deduced h2520-59 amino acid sequence indicated that the polypeptide contains a putative ser/thr kinase domain toward the C-terminus. To determine if h2520-59 polypeptide exhibits ser/thr kinase enzymatic activity, phosphorylation studies are performed. These studies are carried out within host cells stably expressing the h2520-59 nucleotide as described in Example 3.

As described in Papst et al. (J. Biol. Chem., 273: 15077–15084, 1998), COS cells stably expressing h2520-59 nucleic acids are grown in phosphate-free medium containing 10% fetal bovine serum and 150 $\mu$Ci/ml of [$^{32}$P] orthophosphate (30 Ci/mmol). After a 3 hour incubation, the radiolabeled cells are lysed in lysis buffer (25 mM Tris-HCl (pH 7.4), 50 mM NaCl, 0.5% sodium deoxycholate, 2% Nonidet P-40, 0.2% SDS, 1 μM PMSF, 50 μg/ml aprotinin, 50 μM leupeptin). The lysates are immunoprecipitated with either a mouse phosphoserine or mouse phosphothreonine monoclonal antibody (Calbiochem, San Diego, Calif.). The immunoprecipitates are separated on a 7.5% SDS-polyacrylamide gel and the radiolabeled proteins are visualized by autoradiography.

If h2520-59 polypeptide exhibits ser/thr kinase activity, those cells overexpressing h2520-59 polypeptide will have elevated levels of phosphorylated proteins as compared to untransfected COS cells. Immunoprecipitation with antibodies specific for phosphoserine or phosphothreonine will demonstrate that h2520-59 polypeptide phosphorylates serine and threonine residues.

EXAMPLE 6

Kinase Activity of h2520-59 Polypeptides

The kinase activity of h2520-59 is measured by the phosphorylation of a substrate using conventional techniques known in the art, such as the use of gamma-labeled $^{32}$P-ATP and quantitation of the incorporated radioactivity (gamma phosphates) in the substrate using a gamma radioisotope counter. The protein kinase is incubated with a substrate, $^{32}$P-ATP, and a kinase buffer (e.g., 40 mM Hepes-HCl pH 8.0, 2.0 mM DTT, 0.1 mM EGTA, 5 mM magnesium acetate) for 30 minutes. The $^{32}$P incorporated into the substrate is then separated from free $^{32}$P-ATP by conventional electrophoresis (e.g., SDS-PAGE), and the incorporated $^{32}$P is detected, such as by counting in the gamma counter or visualizing it by exposure to x-ray film. Phosphorylation of specific amino acid residues within the substrate is determined by phosphoaminoacid analysis of the hydrolyzed protein as described by Boyle et al., *Methods. Enzymol.* 201:110–148, 1991. Methods for finding additional family members are found in references as follows: Hanks and Quinn, *Methods. Enzymol.* 200:38–62, 1991; Hardie et al., *The Protein Kinase Facts Book, pp* 7–47, 1995; Hanks and Hunter, FASEB 9(8): 576–96, 1995. Alternatively, the serine/threonine kinase activity of h2520-59 can be determined by using a Phospho-Serine/Threonine Assay Kit (Luminex Corporation, Austin, Tex.; Upstate Biotechnology, Waltham, Mass.). These assays utilize myelin basic protein (MBP) as a substrate covalently linked to a fluorescent bead set. After the kinase reaction, phosphorylated MBP is detected by adding a mixture of two phosphoserine/phosphothreonine monoclonal antibodies followed by a biotinylated secondary antibody and a streptavidin-phycoerythrin conjugate. Mean fluorescence intensity is determined according to manufacturer's instructions.

EXAMPLE 7

Upregulated Expression of h2520-59 Protein and mRNA in Various Cancers

Expression of the h2520-59 polypeptide was detected by Western blot analysis using three antibodies raised against each of three short peptide fragments (ELDDNLDTERPVQKRARSGPQPRLC, SEQ ID NO: 13; GPYVLLEPEEGGRAYQALHCPTGTE, SEQ ID NO: 14; RSHLWEAAQVVPDGLGLDEAREEEC, SEQ ID NO: 15) generally corresponding to amino acids 2043, 69–93, and 326–349, respectively, of the h2520-59 polypeptide sequence (SEQ ID NO: 2). The three antibodies were mixed in equal concentrations by volume for use as a Western blot probe. Western blots were carried out using standard techniques on lysates from the following human cell lines, most available from the ATCC with one noted exception: osteosarcoma cells (U-2OS, ATCC Accession No. HTB-96), U-2OS cells transfected with h2520-59 (positive control), lung carcinoma cells (A549, ATCC Accession No. CCL-185), colorectal carcinoma cells (Colo 205, ATCC Accession No. CCL-222; and HCT 116, ATCC Accession No. CCL-247), fibrosarcoma cells (HT-1080, ATCC Accession No. CCL-121), breast adenocarcinoma cells (MDA-MB-231, ATCC Accession No. HTB-26; MDA-MB-468, ATCC Accession No. HTB-132; and SK-BR-3, ATCC Accession No. HTB-30), pancreatic carcinoma cells (MiaPaca-2, ATCC Accession No. CRL-1420), prostate adenocarcinoma cells (PC-3, ATCC Accession No. CRL-1435), ovarian adenocarcinoma cells (SKOV-3, ATCC Accession No. HTB-77), human non-fetal skin fibroblast cells (AG01523A, Coriell Cell Repositories, Camden, N.J.), and a fibrocystic breast cell line (MCF 10A, ATCC Accession No. CRL-10317). The presence of the h2520-59 polypeptide was detected in two of the breast cancer cell lines, MDA-MB-468 and SKBR-3, as well as in the positive control. Non-transfected U2-OS cells did not express h2520-59.

In situ hybridization analysis, using a fill-length open reading frame h2520-59 cDNA probe and standard techniques, determined that the transcription of h2520-59 mRNA was upregulated in tumor sections of human lung cancer, colon cancer, and breast cancer cells that had metastasized to the brain.

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. An isolated nucleic acid molecule comprising a nucleotide sequence selected from the group consisting of:
   (a) the nucleotide sequence set forth in SEQ ID NO: 1;
   (b) a polynucleotide comprising nucleotides 49-1122 of SEQ ID NO 1;
   (c) a nucleotide sequence encoding the polypeptide set forth in SEQ ID NO: 2; and
   (d) a nucleotide sequence complementary to any of (a)–(c).

2. A vector comprising the nucleic acid molecule of claim 1.

3. A host cell comprising the vector of claim 2.

4. A process of producing an h2520-59 polypeptide comprising culturing the host cell of claim 3 under suitable conditions to express the polypeptide, and optionally isolating the polypeptide from the culture.

5. The process of claim 4, wherein the nucleic acid molecule comprises promoter DNA other than the promoter DNA for the native h2520-59 polypeptide operatively linked to the nucleotide sequence encoding the h2520-59 polypeptide.

6. A composition comprising a nucleic acid molecule of claim 1 and a pharmaceutically acceptable formulation agent.

7. The composition of claim 6 wherein said nucleic acid molecule is contained in a viral vector.

8. A viral vector comprising a nucleic acid molecule of claim 1.

9. A method of diagnosing a pathological condition or a susceptibility to a pathological condition in a subject caused by or resulting from a change in level of expression of an h2520-59 polynucleotide comprising:
   (a) determining the presence or amount of expression of said h2520-59 polynucleotide, utilizing polynucleotides of claim 1 in a biological tissue or celluar sample; and
   (b) comparing the level of h2520-59 polynucleotide expression in said biological tissue or cellular sample with those from normal subjects or the subject at a different time, wherein susceptibility to a pathological condition is based on a change in levels of expression of the polynucleotide.

10. A diagnostic reagent comprising a detectably labeled polynucleotide encoding the amino acid sequence set forth in SEQ ID NO: 2.

11. The diagnostic reagent of claim 10, wherein said labeled polynucleotide is a first-strand cDNA.

12. A method for detecting the presence of a nucleic acid molecule encoding an h2520-59 polypeptide in a biological sample comprising the steps of:

(a) providing a biological sample suspected of containing a nucleic molecule encoding an h2520-59 polypeptide;

(b) contacting the biological sample with a diagnostic reagent according to claim 10 under conditions wherein the diagnostic reagent will hybridize with a nucleic acid molecule encoding an h2520-59 polypeptide contained in said biological sample; and (c) detecting the presence of hybridization between a nucleic acid molecule encoding an h2520-59 polypeptide in the biological sample and the diagnostic reagent.

13. A method for detecting a chance in expression of a nucleic acid molecule encoding an h2520-59 polypeptide in a biological sample comprising the steps of:

(a) providing a biological sample suspected of containing a nucleic acid molecule encoding an h2520-59 polypeptide;

(b) contacting the biological sample with a diagnostic reagent according to claim 10 under conditions wherein the diagnostic reagent will hybridize with a nucleic acid molecule encoding an h2520-59 polypeptide;

(c) detecting hybridization between a nucleic acid molecule encoding an h2520-59 polypeptide in the biological sample and the diagnostic reagent; and (d) comparing the level of hybridization between the biological sample and diagnostic reagent with the level of hybridization between a known concentration of a nucleic acid molecule encoding an h2520-59 polypeptide and the diagnostic reagent.

14. The method of claim 12 or 13 wherein said nucleic acid molecule is DNA.

15. The method of claim 12 or 13 wherein said nucleic acid molecule is RNA.

16. A polynucleotide according to claim 1 attached to a solid support.

17. An array of polynucleotides comprising at least one polynucleotide according to claim 1.

* * * * *

UNITED STATES PATENT AND TRADEMARK OFFICE
CERTIFICATE OF CORRECTION

| | |
|---|---|
| PATENT NO. | : 6,881,542 B1 |
| APPLICATION NO. | : 09/909474 |
| DATED | : April 19, 2005 |
| INVENTOR(S) | : John F. Boylan et al. |

It is certified that error appears in the above-identified patent and that said Letters Patent is hereby corrected as shown below:

In the Specification:

At Column 2, line 14, "shown be" should be -- shown to be --.

At Column 3, line 49, "(a)-(f)" should be -- (a)-(f), --.

At Column 7, line 29, "ofh2520-59" should be -- of h2520-59 --.

At Column 7, line 30, "steps of." should be -- steps of: --.

At Column 7, line 46, "ofh2520-59" should be -- of h2520-59 --.

At Column 8, line 20, "herein;" should be -- herein. --.

At Column 8, line 42, "depicts" should be -- depict --.

At Column 9, line 38, "2," should be -- 2. --.

At Column 11, line 57, "N-6" should be -- N6 --.

At Column 11, line 61, "N6 iso-" should be -- N6-iso- --.

At Column 13, line 52, "Ed," should be -- Ed., --.

At Column 13, line 53, "(1989)" should be -- (1989)) --.

At Column 14, line 16, "Na-" should be -- Na+ --.

At Column 15, line 24, "normative" should be -- nonnative --.

At Column 20, line 17, "Pat. 5,808,029" should be -- Pat. No. 5,808,029 --.

At Column 21, line 30, "protein" should be -- Protein --.

At Column 21, line 32, "Sci" should be -- Sci. --.

At Column 21, line 41, "1992);" should be -- 1992; --.

At Column 24, line 59, "apart" should be -- a part --.

UNITED STATES PATENT AND TRADEMARK OFFICE
CERTIFICATE OF CORRECTION

PATENT NO. : 6,881,542 B1
APPLICATION NO. : 09/909474
DATED : April 19, 2005
INVENTOR(S) : John F. Boylan et al.

It is certified that error appears in the above-identified patent and that said Letters Patent is hereby corrected as shown below:

At Column 28, line 12, "Devel," should be -- Devel., --.

At Column 28, line 17, "Devel," should be -- Devel., --.

At Column 29, line 2, "La Jolla" should be -- La Jolla, --.

At Column 29, line 20, "Sanbrook" should be -- Sambrook --.

At Column 31, line 23, "of a." should be -- of a chaotrope --.

At Column 31, line 24, "chaotrope" should be -- a chaotrope --.

At Column 32, line 3, "elctrophoresis" should be -- electrophoresis --.

At Column 32, line 4, "elctrophoresis" should be -- electrophoresis --.

At Column 33, line 54, "polyoxyetbylated" should be -- polyoxyethylated --.

At Column 35, line 35, "labeled thousands" should be -- labeled cDNA which is specifically bound to each target DNA. In this way, the expression of thousands --.

At Column 38, line 42, "binding" should be -- binding --.

At Column 39, line 30, "1h2520-59" should be -- h2520-59 --.

At Column 43, line 1, "mesenchyrnoma" should be -- mesenchymoma --.

At Column 43, line 21, "careniosarcoma" should be -- carcinosarcoma --.

At Column 52, line 25, "pararnyxovirus" should be -- paramyxovirus --.

At Column 53, line 17, "flag" should be -- flanking --.

At Column 53, line 67, "intronlextron" should be -- intron/extron --.

At Column 54, line 14, "tissue orbodily" should be -- tissue or bodily --.

At Column 54, line 35, "b2520-59" should be -- h2520-59 --.

At Column 55, line 32, "Phammacia" should be -- Pharmacia --.

UNITED STATES PATENT AND TRADEMARK OFFICE
CERTIFICATE OF CORRECTION

PATENT NO. : 6,881,542 B1
APPLICATION NO. : 09/909474
DATED : April 19, 2005
INVENTOR(S) : John F. Boylan et al.

It is certified that error appears in the above-identified patent and that said Letters Patent is hereby corrected as shown below:

At Column 56, line 41, "Carlsbad" should be -- Carlsbad, --.

At Column 57, line 5, "Ts panel" should be -- This panel --.

At Column 60, line 11, "2043" should be -- 20-43 --.

At Column 60, line 40, "fill-length" should be -- full-length --.

Signed and Sealed this

Twenty-eighth Day of August, 2007

JON W. DUDAS
*Director of the United States Patent and Trademark Office*

SEQUENCE LISTING

```
<160> NUMBER OF SEQ ID NOS: 15

<210> SEQ ID NO 1
<211> LENGTH: 2059
<212> TYPE: DNA
<213> ORGANISM: Homo sapiens
<220> FEATURE:
<221> NAME/KEY: CDS
<222> LOCATION: (49)..(1122)
```

<400> SEQUENCE: 1

| | | |
|---|---|---|
| gctctgagcc ccggcggcgc ccgggcccac gcggaacgac ggggcgag atg cga gcc<br>                                                                                                    Met Arg Ala<br>                                                                                                     1 | 57 |
| acc cct ctg gct gct cct gcg ggt tcc ctg tcc agg aag aag cgg ttg<br>Thr Pro Leu Ala Ala Pro Ala Gly Ser Leu Ser Arg Lys Lys Arg Leu<br>    5                        10                      15 | 105 |
| gag ttg gat gac aac tta gat acc gag cgt ccc gtc cag aaa cga gct<br>Glu Leu Asp Asp Asn Leu Asp Thr Glu Arg Pro Val Gln Lys Arg Ala<br> 20                        25                      30                      35 | 153 |
| cga agt ggg ccc cag ccc aga ctg ccc ccc tgc ctg ttg ccc ctg agc<br>Arg Ser Gly Pro Gln Pro Arg Leu Pro Pro Cys Leu Leu Pro Leu Ser<br>                40                      45                      50 | 201 |
| cca cct act gct cca gat cgt gca act gct gtg gcc act gcc tcc cgt<br>Pro Pro Thr Ala Pro Asp Arg Ala Thr Ala Val Ala Thr Ala Ser Arg<br>        55                      60                      65 | 249 |
| ctt ggg ccc tat gtc ctc ctg gag ccc gag gag ggc ggg cgg gcc tac<br>Leu Gly Pro Tyr Val Leu Leu Glu Pro Glu Glu Gly Gly Arg Ala Tyr<br>            70                      75                      80 | 297 |
| cgg gcc ctg cac tgc cct aca ggc act gag tat acc tgc aag gtg tac<br>Arg Ala Leu His Cys Pro Thr Gly Thr Glu Tyr Thr Cys Lys Val Tyr<br> 85                        90                      95 | 345 |
| ccc gtc cag gaa gcc ctg gcc gtg ctg gag ccc tac gcg cgg ctg ccc<br>Pro Val Gln Glu Ala Leu Ala Val Leu Glu Pro Tyr Ala Arg Leu Pro<br>100                       105                    110                  115 | 393 |
| ccg cac aag cat gtg gct cgg ccc act gag gtc ctg gct ggt acc cag<br>Pro His Lys His Val Ala Arg Pro Thr Glu Val Leu Ala Gly Thr Gln<br>                120                    125                    130 | 441 |
| ctc ctc tac gcc ttt ttc act cgg acc cat ggg gac atg cac agc ctg<br>Leu Leu Tyr Ala Phe Phe Thr Arg Thr His Gly Asp Met His Ser Leu<br>          135                    140                    145 | 489 |
| gtg cga agc cgc cac cgt atc cct gag cct gag gct gcc gtg ctc ttc<br>Val Arg Ser Arg His Arg Ile Pro Glu Pro Glu Ala Ala Val Leu Phe<br>150                       155                    160 | 537 |
| cgc cag atg gcc acc gcc ctg gcg cac tgt cac cag cac ggt ctg gtc<br>Arg Gln Met Ala Thr Ala Leu Ala His Cys His Gln His Gly Leu Val<br>     165                    170                    175 | 585 |
| ctg cgt gat ctc aag ctg tgt cgc ttt gtc ttc gct gac cgt gag agg<br>Leu Arg Asp Leu Lys Leu Cys Arg Phe Val Phe Ala Asp Arg Glu Arg<br>180                       185                    190                  195 | 633 |
| aag aag ctg gtg ctg gag aac ctg gag gac tcc tgc gtg ctg act ggg<br>Lys Lys Leu Val Leu Glu Asn Leu Glu Asp Ser Cys Val Leu Thr Gly<br>                200                    205                    210 | 681 |
| cca gat gat tcc ctg tgg gac aag cac gcg tgc cca gcc tac gtg gga<br>Pro Asp Asp Ser Leu Trp Asp Lys His Ala Cys Pro Ala Tyr Val Gly<br>          215                    220                    225 | 729 |
| cct gag ata ctc agc tca cgg gcc tca tac tcg ggc aag gca gcc gat<br>Pro Glu Ile Leu Ser Ser Arg Ala Ser Tyr Ser Gly Lys Ala Ala Asp<br>230                       235                    240 | 777 |
| gtc tgg agc ctg ggc gtg gcg ctc ttc acc atg ctg gcc ggc cac tac<br>Val Trp Ser Leu Gly Val Ala Leu Phe Thr Met Leu Ala Gly His Tyr<br>     245                    250                    255 | 825 |
| ccc ttc cag gac tcg gag cct gtc ctg ctc ttc ggc aag atc cgc cgc<br>Pro Phe Gln Asp Ser Glu Pro Val Leu Leu Phe Gly Lys Ile Arg Arg<br>260                       265                    270                  275 | 873 |
| ggg gcc tac gcc ttg cct gca ggc ctc tcg gcc cct gcc cgc tgt ctg<br>Gly Ala Tyr Ala Leu Pro Ala Gly Leu Ser Ala Pro Ala Arg Cys Leu<br>                280                    285                    290 | 921 |

-continued

```
gtt cgc tgc ctc ctt cgt cgg gag cca gct gaa cgg ctc aca gcc aca      969
Val Arg Cys Leu Leu Arg Arg Glu Pro Ala Glu Arg Leu Thr Ala Thr
            295                 300                 305 ggc atc ctc ctg cac ccc tgg ctg cga cag gac ccg atg ccc tta gcc     1017
Gly Ile Leu Leu His Pro Trp Leu Arg Gln Asp Pro Met Pro Leu Ala
        310                 315                 320 cca acc cga tcc cat ctc tgg gag gct gcc cag gtg gtc cct gat gga     1065
Pro Thr Arg Ser His Leu Trp Glu Ala Ala Gln Val Val Pro Asp Gly
    325                 330                 335 ctg ggg ctg gac gaa gcc agg gaa gag gag gga gac aga gaa gtg gtt     1113
Leu Gly Leu Asp Glu Ala Arg Glu Glu Glu Gly Asp Arg Glu Val Val
340                 345                 350                 355 ctg tat ggc taggaccacc ctactacacg ctcagctgcc aacagtggat             1162
Leu Tyr Gly tgagtttggg ggtagctcca agccttctcc tgcctctgaa ctgagccaaa ccttcagtgc   1222
cttccagaag ggagaaaggc agaagcctgt gtggagtgtg ctgtgtacac atctgctttg   1282
ttccacacac atgcagttcc tgcttgggtg cttatcaggt gccaagccct gttctcggtg   1342
ctgggagtac agcagtgagc aaaggagaca atattcsctg ctcacagaga tgacaaactg   1402
gcatccttga gctgacaaca cttttccatg accataggtc actgtctaca ctgggtacac   1462
tttgtaccag tgtcggcctc cactgatgct ggtgctcagg cacctctgtc caaggacaat   1522 cccttttcaca aacaaaccag ctgcctttgt atcttgtacc ttttcagaga aagggaggta   1582
tccctgtgcc aaaggctcca ggcctctccc ctgcaactca ggacccaagc ccagctcact   1642
ctgggaactg tgttcccagc atctctgtcc tcttgattaa gagattctcc ttccaggcct   1702
aagcctggga tttgggccag agataagaat ccaaactatg aggctagttc ttgtctaact   1762
caagactgtt ctggaatgag ggtccaggcc tgtcaaccat ggggcttctg acctgagcac   1822
caaggttgag ggacaggatt aggcagggtc tgtcctgtgg ccacctggaa agtcccaggt   1882
gggactcttc tggggacact tggggtccac aatcccaggt ccatactcta ggttttggat   1942
accatgagta tgtatgttta cctgtgccta ataaggaga attatgaaat aaaaaaaaaa    2002
aaaaaaaaaa aaaaaaaaaa aaaaaaaaaa aaaaaaaaaa aaaaaaa                 2059
```

<210> SEQ ID NO 2
<211> LENGTH: 358
<212> TYPE: PRT
<213> ORGANISM: Homo sapiens

<400> SEQUENCE: 2

```
Met Arg Ala Thr Pro Leu Ala Ala Pro Ala Gly Ser Leu Ser Arg Lys
1               5                   10                  15

Lys Arg Leu Glu Leu Asp Asp Asn Leu Asp Thr Glu Arg Pro Val Gln
            20                  25                  30

Lys Arg Ala Arg Ser Gly Pro Gln Pro Arg Leu Pro Pro Cys Leu Leu
        35                  40                  45

Pro Leu Ser Pro Pro Thr Ala Pro Asp Arg Ala Thr Ala Val Ala Thr
    50                  55                  60

Ala Ser Arg Leu Gly Pro Tyr Val Leu Leu Glu Pro Glu Glu Gly Gly
65                  70                  75                  80

Arg Ala Tyr Arg Ala Leu His Cys Pro Thr Gly Thr Glu Tyr Thr Cys
                85                  90                  95

Lys Val Tyr Pro Val Gln Glu Ala Leu Ala Val Leu Glu Pro Tyr Ala
            100                 105                 110
```

```
Arg Leu Pro Pro His Lys His Val Ala Arg Pro Thr Glu Val Leu Ala
        115                 120                 125

Gly Thr Gln Leu Leu Tyr Ala Phe Phe Thr Arg Thr His Gly Asp Met
    130                 135                 140

His Ser Leu Val Arg Ser Arg His Arg Ile Pro Glu Pro Glu Ala Ala
145                 150                 155                 160

Val Leu Phe Arg Gln Met Ala Thr Ala Leu Ala His Cys His Gln His
                165                 170                 175

Gly Leu Val Leu Arg Asp Leu Lys Leu Cys Arg Phe Val Phe Ala Asp
            180                 185                 190

Arg Glu Arg Lys Lys Leu Val Leu Glu Asn Leu Glu Asp Ser Cys Val
        195                 200                 205

Leu Thr Gly Pro Asp Asp Ser Leu Trp Asp Lys His Ala Cys Pro Ala
    210                 215                 220

Tyr Val Gly Pro Glu Ile Leu Ser Ser Arg Ala Ser Tyr Ser Gly Lys
225                 230                 235                 240

Ala Ala Asp Val Trp Ser Leu Gly Val Ala Leu Phe Thr Met Leu Ala
                245                 250                 255

Gly His Tyr Pro Phe Gln Asp Ser Glu Pro Val Leu Leu Phe Gly Lys
            260                 265                 270

Ile Arg Arg Gly Ala Tyr Ala Leu Pro Ala Gly Leu Ser Ala Pro Ala
        275                 280                 285

Arg Cys Leu Val Arg Cys Leu Leu Arg Arg Glu Pro Ala Glu Arg Leu
    290                 295                 300

Thr Ala Thr Gly Ile Leu Leu His Pro Trp Leu Arg Gln Asp Pro Met
305                 310                 315                 320

Pro Leu Ala Pro Thr Arg Ser His Leu Trp Glu Ala Ala Gln Val Val
                325                 330                 335

Pro Asp Gly Leu Gly Leu Asp Glu Ala Arg Glu Glu Gly Asp Arg
            340                 345                 350

Glu Val Val Leu Tyr Gly
        355

<210> SEQ ID NO 3
<211> LENGTH: 21
<212> TYPE: DNA
<213> ORGANISM: Artificial Sequence
<220> FEATURE:
<223> OTHER INFORMATION: PCR Primer

<400> SEQUENCE: 3
tggtgctgga gaacctggag g                                           21

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
cgagtcctgg aagggtagt g                                            21

<210> SEQ ID NO 5
<211> LENGTH: 11
<212> TYPE: PRT
<213> ORGANISM: Artificial Sequence
<220> FEATURE:
<223> OTHER INFORMATION: HIV TAT peptide
```

```
<400> SEQUENCE: 5

Tyr Gly Arg Lys Lys Arg Arg Gln Arg Arg
1               5                   10

<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6
cggggcgaga tgcgagccac                                                     20

<210> SEQ ID NO 7
<211> LENGTH: 20
<212> TYPE: DNA
<213> ORGANISM: Artificial Sequence
<220> FEATURE:
<223> OTHER INFORMATION: PCR Primer

<400> SEQUENCE: 7
agggtggtcc tagccataca                                                     20

<210> SEQ ID NO 8
<211> LENGTH: 358
<212> TYPE: PRT
<213> ORGANISM: Homo sapiens

<400> SEQUENCE: 8

Met Arg Ala Thr Pro Leu Ala Ala Pro Ala Gly Ser Leu Ser Arg Lys
1               5                   10                  15

Lys Arg Leu Glu Leu Asp Asp Asn Leu Asp Thr Glu Arg Pro Val Gln
            20                  25                  30

Lys Arg Ala Arg Ser Gly Pro Gln Pro Arg Leu Pro Pro Cys Leu Leu
        35                  40                  45

Pro Leu Ser Pro Pro Thr Ala Pro Asp Arg Ala Thr Ala Val Ala Thr
    50                  55                  60

Ala Ser Arg Leu Gly Pro Tyr Val Leu Leu Glu Pro Glu Glu Gly Gly
65                  70                  75                  80

Arg Ala Tyr Gln Ala Leu His Cys Pro Thr Gly Thr Glu Tyr Thr Cys
                85                  90                  95

Lys Val Tyr Pro Val Gln Glu Ala Pro Ala Val Leu Glu Pro Tyr Ala
            100                 105                 110

Arg Leu Pro Pro His Lys His Val Ala Arg Pro Thr Glu Val Leu Ala
        115                 120                 125

Gly Thr Gln Leu Leu Tyr Ala Phe Phe Thr Arg Thr His Gly Asp Met
    130                 135                 140

His Ser Leu Val Arg Ser Arg His Arg Ile Pro Glu Pro Glu Ala Ala
145                 150                 155                 160

Val Leu Phe Arg Gln Met Ala Thr Ala Leu Ala His Cys His Gln His
                165                 170                 175

Gly Leu Val Leu Arg Asp Leu Lys Leu Cys Arg Phe Val Phe Ala Asp
            180                 185                 190

Arg Glu Arg Lys Lys Leu Val Leu Glu Asn Leu Glu Asp Ser Cys Val
        195                 200                 205

Leu Thr Gly Pro Asp Asp Ser Leu Trp Asp Lys His Ala Cys Pro Ala
    210                 215                 220
```

-continued

```
Tyr Val Gly Pro Glu Ile Leu Ser Ser Arg Ala Ser Tyr Ser Gly Lys
225                 230                 235                 240

Ala Ala Asp Val Trp Ser Leu Gly Val Ala Leu Phe Thr Met Leu Ala
            245                 250                 255

Gly His Tyr Pro Phe Gln Asp Ser Glu Pro Val Leu Leu Phe Gly Lys
            260                 265                 270

Ile Arg Arg Gly Ala Tyr Ala Leu Pro Ala Gly Leu Ser Ala Pro Ala
            275                 280                 285

Arg Cys Leu Val Arg Cys Leu Leu Arg Arg Glu Pro Ala Glu Arg Leu
        290                 295                 300

Thr Ala Thr Gly Ile Leu Leu His Pro Trp Leu Arg Gln Asp Pro Met
305                 310                 315                 320

Pro Leu Ala Pro Thr Arg Ser His Leu Trp Glu Ala Ala Gln Val Val
                325                 330                 335

Pro Asp Gly Leu Gly Leu Asp Glu Ala Arg Glu Glu Glu Gly Asp Arg
            340                 345                 350

Glu Val Val Leu Tyr Gly
            355
```

<210> SEQ ID NO 9
<211> LENGTH: 153
<212> TYPE: PRT
<213> ORGANISM: Homo sapiens
<220> FEATURE:
<221> NAME/KEY: misc_feature
<222> LOCATION: (136)
<223> OTHER INFORMATION: Xaa = unknown or other
<220> FEATURE:
<221> NAME/KEY: misc_feature
<222> LOCATION: (138)
<223> OTHER INFORMATION: Xaa = unknown or other
<220> FEATURE:
<221> NAME/KEY: misc_feature
<222> LOCATION: (141)
<223> OTHER INFORMATION: Xaa = unknown or other
<220> FEATURE:
<221> NAME/KEY: misc_feature
<222> LOCATION: (142)
<223> OTHER INFORMATION: Xaa = unknown or other
<220> FEATURE:
<221> NAME/KEY: misc_feature
<222> LOCATION: (143)
<223> OTHER INFORMATION: Xaa = unknown or other
<220> FEATURE:
<221> NAME/KEY: misc_feature
<222> LOCATION: (152)
<223> OTHER INFORMATION: Xaa = unknown or other

<400> SEQUENCE: 9

```
Leu Arg Phe Ala Ser Pro Gly Pro Gly Ala Gly Arg Ala Arg Asp Ser
1               5                   10                  15

Gln Arg Lys Trp Arg Arg Leu Arg Ala Arg Pro Leu Leu Gly Pro Gly
            20                  25                  30

Gln Gly Trp Ser Trp Ala Gly Ile Pro Ser Ser Ala Ala Ala Gln Arg
        35                  40                  45

Ala Gly Pro Pro Ala Gly Ala Leu Glu Ala Leu Ser Pro Gly Gly Ala
50                  55                  60

Arg Ala His Ala Glu Arg Arg Gly Glu Met Arg Ala Thr Pro Leu Ala
65                  70                  75                  80

Ala Pro Ala Gly Ser Leu Ser Arg Lys Lys Arg Leu Glu Leu Asp Asp
                85                  90                  95

Asn Leu Asp Thr Glu Arg Pro Val Gln Lys Arg Ala Arg Ser Gly Pro
            100                 105                 110
```

```
Gln Pro Arg Leu Pro Pro Cys Leu Leu Pro Leu Ser Pro Pro Thr Ala
            115                 120                 125

Pro Asp Arg Ala Thr Ala Val Xaa Thr Xaa Ser Arg Xaa Xaa Xaa Tyr
130                 135                 140

Val Leu Leu Glu Ala Arg Arg Xaa Ala
145                 150

<210> SEQ ID NO 10
<211> LENGTH: 233
<212> TYPE: PRT
<213> ORGANISM: Homo sapiens

<400> SEQUENCE: 10

Gly Pro Gly Trp Tyr Pro Ala Pro Leu Arg Leu Phe His Ser Asp Pro
1               5                   10                  15

Trp Gly His Ala Gln Pro Gly Ala Lys Arg His Arg Ile Pro Glu Pro
            20                  25                  30

Glu Ala Ala Val Leu Phe Arg Gln Met Ala Thr Ala Leu Ala His Cys
        35                  40                  45

His Gln His Gly Leu Val Leu Arg Asp Leu Lys Leu Cys Arg Phe Val
    50                  55                  60

Phe Ala Asp Arg Glu Arg Lys Lys Leu Val Leu Glu Asn Leu Glu Asp
65                  70                  75                  80

Ser Cys Val Leu Thr Gly Pro Asp Asp Ser Leu Trp Asp Lys His Ala
                85                  90                  95

Cys Pro Ala Tyr Val Gly Pro Glu Ile Leu Ser Ser Arg Ala Ser Tyr
            100                 105                 110

Ser Gly Lys Ala Ala Asp Val Trp Ser Leu Gly Val Ala Leu Phe Thr
        115                 120                 125

Met Leu Ala Gly His Tyr Pro Phe Gln Asp Ser Glu Pro Val Leu Leu
    130                 135                 140

Phe Gly Lys Ile Arg Arg Gly Ala Tyr Ala Leu Pro Ala Gly Leu Ser
145                 150                 155                 160

Ala Pro Ala Arg Cys Leu Val Arg Cys Leu Leu Arg Arg Glu Pro Ala
                165                 170                 175

Glu Arg Leu Thr Ala Thr Gly Ile Leu Leu His Pro Trp Leu Arg Gln
            180                 185                 190

Asp Pro Met Pro Leu Ala Pro Thr Arg Ser His Leu Trp Glu Ala Ala
        195                 200                 205

Gln Val Val Pro Asp Gly Leu Gly Leu Asp Glu Ala Arg Glu Glu Glu
    210                 215                 220

Gly Asp Arg Glu Val Val Leu Tyr Gly
225                 230

<210> SEQ ID NO 11
<211> LENGTH: 360
<212> TYPE: PRT
<213> ORGANISM: Homo sapiens

<400> SEQUENCE: 11

Gly Gln Gly Trp Ser Trp Ala Gly Ile Pro Ser Ser Ala Ala Ala Gln
1               5                   10                  15

Arg Ala Gly Pro Pro Ala Gly Ala Leu Glu Ala Leu Ser Pro Gly Gly
            20                  25                  30

Ala Arg Ala His Ala Glu Arg Arg Gly Glu Met Arg Ala Thr Pro Leu
        35                  40                  45
```

```
Ala Ala Pro Ala Gly Ser Leu Ser Arg Lys Lys Arg Leu Glu Leu Asp
            50              55                  60
Asp Asn Leu Asp Thr Glu Arg Pro Val Gln Lys Arg Ala Arg Ser Gly
 65                  70                  75                  80
Pro Gln Pro Arg Leu Pro Pro Cys Leu Leu Pro Leu Ser Pro Pro Thr
                85                  90                  95
Ala Pro Asp Arg Ala Thr Ala Val Ala Thr Ala Ser Arg Leu Gly Pro
            100                 105                 110
Tyr Val Leu Leu Glu Pro Glu Gly Gly Arg Ala Tyr Gln Ala Leu
            115                 120                 125
His Cys Pro Thr Gly Thr Glu Tyr Thr Cys Lys Val Tyr Pro Val Gln
    130                 135                 140
Glu Ala Leu Ala Val Leu Glu Pro Tyr Ala Arg Leu Pro Pro His Lys
145                 150                 155                 160
His Val Ala Arg Pro Thr Glu Val Leu Ala Gly Thr Gln Leu Leu Tyr
                165                 170                 175
Ala Phe Phe Thr Arg Thr His Gly Asp Met His Ser Leu Val Arg Ser
            180                 185                 190
Arg His Arg Ile Pro Glu Pro Glu Ala Ala Val Leu Phe Arg Gln Met
        195                 200                 205
Ala Thr Ala Leu Ala His Cys His Gln His Gly Leu Val Leu Arg Asp
    210                 215                 220
Leu Lys Leu Cys Arg Phe Val Phe Ala Asp Arg Glu Arg Lys Lys Leu
225                 230                 235                 240
Val Leu Glu Asn Leu Glu Asp Ser Cys Val Leu Thr Gly Pro Asp Asp
                245                 250                 255
Ser Leu Trp Asp Lys His Ala Cys Pro Ala Tyr Val Gly Pro Glu Ile
            260                 265                 270
Leu Ser Ser Arg Ala Ser Tyr Ser Gly Lys Ala Ala Asp Val Trp Ser
        275                 280                 285
Leu Gly Val Ala Leu Phe Thr Met Leu Ala Gly His Tyr Pro Phe Gln
    290                 295                 300
Asp Ser Glu Pro Val Leu Leu Phe Gly Lys Ile Arg Arg Gly Ala Tyr
305                 310                 315                 320
Ala Leu Pro Ala Gly Leu Ser Ala Pro Ala Arg Cys Leu Val Arg Cys
                325                 330                 335
Leu Leu Arg Arg Glu Pro Ala Glu Arg Leu Thr Ala Thr Gly Ile Leu
            340                 345                 350
Leu His Pro Trp Leu Arg Gln Asp
        355                 360
```

<210> SEQ ID NO 12
<211> LENGTH: 510
<212> TYPE: DNA
<213> ORGANISM: Homo sapiens

<400> SEQUENCE: 12

```
ccttctgttt ctccccatgt cccaggaaga agctggtgct ggagaacctg gaggactcct    60
gcgtgctgac tgggccagat gattccctgt gggacaagca cgcgtgccca gcctacgtgg   120
gacctgagat actcagctca cgggcctcat actcgggcaa ggcagccgat gtctggagcc   180
tgggcgtggc gctcttcacc atgctggccg gccactaccc cttccaggac tcggagcctg   240
tcctgctctt cggcaagatc cgccgcgggg cctacgcctt gcctgcaggc ctctcggccc   300
ctgcccgctg tctggttcgc tgcctccttc gtcgggagcc agctgaacgg ctcacagcca   360
```

```
caggcatcct cctgcacccc tggctgcgac aggacccgat gcccttagcc ccaacccgat    420
cccatctctg ggaggctgcc caggtggtcc ctgatggact ggggctggac gaagccaggg    480
aagaggaggg agacagagaa gtggttctgt                                    510
```

```
<210> SEQ ID NO 13
<211> LENGTH: 25
<212> TYPE: PRT
<213> ORGANISM: Homo sapiens

<400> SEQUENCE: 13

Glu Leu Asp Asp Asn Leu Asp Thr Glu Arg Pro Val Gln Lys Arg Ala
1               5                   10                  15

Arg Ser Gly Pro Gln Pro Arg Leu Cys
            20                  25

<210> SEQ ID NO 14
<211> LENGTH: 25
<212> TYPE: PRT
<213> ORGANISM: Homo sapiens

<400> SEQUENCE: 14

Gly Pro Tyr Val Leu Leu Glu Pro Glu Glu Gly Arg Ala Tyr Gln
1               5                   10                  15

Ala Leu His Cys Pro Thr Gly Thr Glu
            20                  25

<210> SEQ ID NO 15
<211> LENGTH: 25
<212> TYPE: PRT
<213> ORGANISM: Homo sapiens

<400> SEQUENCE: 15

Arg Ser His Leu Trp Glu Ala Ala Gln Val Val Pro Asp Gly Leu Gly
1               5                   10                  15

Leu Asp Glu Ala Arg Glu Glu Glu Cys
            20                  25
```